(12) United States Patent
Zhang et al.

(10) Patent No.: US 7,399,767 B2
(45) Date of Patent: Jul. 15, 2008

(54) HETEROCYCLIC BENZO[C]CHROMENE DERIVATIVES USEFUL AS MODULATORS OF THE ESTROGEN RECEPTORS

(75) Inventors: Xuqing Zhang, Exton, PA (US); Xiaojie Li, Green Brook, NJ (US); Zhihua Sui, Exton, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 11/334,603

(22) Filed: Jan. 18, 2006

(65) Prior Publication Data

US 2006/0205741 A1 Sep. 14, 2006

Related U.S. Application Data

(60) Provisional application No. 60/646,007, filed on Jan. 21, 2005.

(51) Int. Cl.
*A01N 43/54* (2006.01)
*C07D 239/42* (2006.01)
*C07D 401/00* (2006.01)
*C07D 401/04* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. ...................... 514/256; 544/333
(58) Field of Classification Search ................ 544/333; 514/256
See application file for complete search history.

(56) References Cited

U.S. PATENT DOCUMENTS 5,958,782 A * 9/1999 Bentsen et al. ................ 436/79
6,844,336 B2 1/2005 Kuenzer et al.

FOREIGN PATENT DOCUMENTS

WO WO 00/39120 A2 7/2000
WO WO 01/68634 A1 9/2001

OTHER PUBLICATIONS

PCT International Search Report for PCT International Appln. No. PCT/US2006/001928 dated Jun. 22, 2006.
Albert, J.L. et al.: "Estrogen Regulation of Placental Alkaline Phosphatase Gene Expression in a Human Endometrial Adenocarcinoma Cell Line[1]"; Cancer Res. (1990), 50(11): 3306-10.
Welshons, W.V. et al.: "Stimulation of breast cancer cells in vitro by the environmental estrogen enterolactone and the phytoestrogen equol"; Breast Cancer Res. Treat. (1987) 10(2): 169-175.
Database Crossfire Beilstein [Online] Beilstein Institut zur Foerderung der chemischen Wissenschaften, Frankfurt am Main, DE; XP002384114 Abstract & Bhandari, P.R. et al: Arch. Pharm. Ber Dtsch. Phar. Ges., (1964) vol. 297, pp. 698-701.
Database Crossfire Beilstein [Online] Beilstein Institut zur Foerderung der chemischen Wissenschaften, Frankfurt am Main, DE; XP002384115 Abstract & Buu-Hoi, N.P. et al.: J. Chem. Soc., (1969) pp. 2069-2070.
Database Crossfire Beilstein [Online] Beilstein Institut zur Foerderung der chemischen Wissenschaften, Frankfurt am Main, DE; XP002384116 Abstract & Moffet, R.B. et al.: J. Med. Chem., (1964) vol. 7, pp. 446-449.
Database Crossfire Beilstein [Online] Beilstein Institut zur Foerderung der chemischen Wissenschaften, Frankfurt am Main, DE; XP002384117 Abstract & Vernin, G. et al.: J. Heterocycl. Chem., (1979) vol. 16, pp. 97-103.

* cited by examiner

*Primary Examiner*—James O. Wilson
*Assistant Examiner*—Erich A Leeser

(57) ABSTRACT

The present invention is directed to novel heterocyclic benzo[c]chromene derivatives, pharmaceutical compositions containing them and their use in the treatment of disorders mediated by one or more estrogen receptors. The compounds of the invention are useful in the treatment of disorders associated with the depletion of estrogen such as hot flashes, vaginal dryness, osteopenia and osteoporosis; hormone sensitive cancers and hyperplasia of the breast, endometrium, cervix and prostate; endometriosis, uterine fibroids, osteoarthritis and as contraceptive agents, alone or in combination with a progestogen or progestogen antagonist.

9 Claims, No Drawings

HETEROCYCLIC BENZO[C]CHROMENE DERIVATIVES USEFUL AS MODULATORS OF THE ESTROGEN RECEPTORS

CROSS REFERENCE TO RELATED APPLICATIONS

This application claims the benefit of U.S. Provisional Application 60/646,007, filed on Jan. 21, 2005, which is incorporated by reference herein in its entirety.

FIELD OF THE INVENTION

The present invention is directed to novel heterocyclic benzo[c]chromene derivatives, pharmaceutical compositions containing them and their use in the treatment or prevention of disorders and diseases mediated by an estrogen receptor such as hot flashes, vaginal dryness, osteopenia, osteoporosis, hyperlipidemia, loss of cognitive function, degenerative brain diseases, cardiovascular diseases, cerebrovascular diseases, hormone sensitive cancers and hyperplasia (in tissues including breast, endometrium, and cervix in women and prostate in men), endometriosis, uterine fibroids, osteoarthritis; and as contraceptive agents either alone or in combination with a progestogen or progestogen antagonist. The compounds of the invention are selective estrogen receptor modulators.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in women's body.

Endogenous estrogens, such as 17β-estradiol and estrone, play a central role in the development of and maintenance of the female sex organs, mammary glands, and other sexual characteristics. In addition to their role as female sex hormone, estrogens are involved in the growth and function of a number of other tissues, such as the cardiovascular system, the central nervous system, and the skeleton, both in females and males. The significance of the estrogens in the development of the female reproductive system led to the development of a variety of compounds that interact with the estrogen receptors, such as contraceptives and agents for treatment of breast cancers. More recently, intensive efforts have focused on the selective estrogen receptor modulators for treatment and prevention of postmenopausal conditions, such as osteoporosis, coronary artery disease, depression and Alzheimer disease.

Menopause is defined as the permanent cessation of menses due to loss of ovarian follicular function and the almost termination of estrogen production. The midlife transition of menopause is characterized by a decrease in estrogen that provokes both short-term and long-term symptoms with the vasomotor, urogenital, cardiovascular, skeletal and central nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy and stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left untreated, the problems can become permanent.

Heart attack and stroke are major causes of morbidity and mortality among senior women. Female morbidity from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure and a decrease of bone strength. Rapid loss of bone mass during the year immediately following menopause leads to postmenopausal osteoporosis and increased risk of fracture.

Estrogen deficiency is also one of the causes for the degenerative changes in the central nervous system and may lead to Alzheimer's disease and decline of cognition. Recent evidence suggests an association between estrogen, menopause and cognition. More particularly, it has been reported that estrogen replacement therapy and the use of estrogen in women may prevent the development of AD and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown significant benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to age of 75 years.

However, there are numerous undesirable effects associated with ERT that reduce patient compliance. Venous thromboembolism, gallbladder disease, resumption of menses, mastodynia and a possible increased risk of developing uterine and/or breast cancer are the risks associated with ERT. Up to 30% of women who were prescribed ERT did not fill the prescription, and the discontinuation rate is between 38% and 70%, with safety concerns and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for arteriosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

SUMMARY OF THE INVENTION

The present invention is directed to a compound of formula (I)

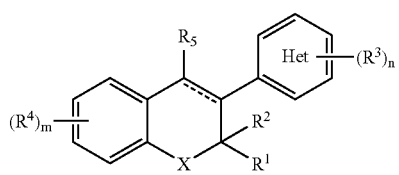

(I)

wherein

- - - - - represents a single or double bond,

X is selected from the group consisting of O and S;

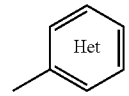

is a six membered heteroaryl ring structure containing one to two nitrogen atoms;

$R^1$ is selected from the group consisting of hydrogen, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^DR^E$, —$NR^DR^E$, $NR^D$—$SO_2$—$R^F$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^DR^E$, $NR^DR^E$, $NR^D$—$SO_2$—$R^F$, -(alkyl)$_{0-4}$-C(O)—$NR^DR^E$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$;

wherein Q is selected from the group consisting of O, S, NH, N(alkyl) and —CH═CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

$R^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^DR^E$, —$NR^DR^E$, $NR^D$—$SO_2$—$R^F$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$;

alternatively, $R^1$ and $R^2$ are taken together with the carbon atom to which they are bound to form C(O);

n is an integer selected from 0 to 4;

each $R^3$ is independently selected from the group consisting of halogen, hydroxy, $R^C$, amino, alkylamino, dialkylamino, nitro, cyano, $SO_2$, —C(O)$R^G$, —C(O)O$R^G$, —OC(O)$R^G$, —OC(O)O$R^G$, —OC(O)N($R^G$)$_2$, —N($R^G$)C(O)$R^G$, —OSi($R^G$)$_3$——O$R^G$, —SO$_2$N($R^G$)$_2$, —O-(alkyl)$^{1-4}$-C(O)$R^G$ and —O-(alkyl)$_{1-4}$-C(O)O$R^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, $R^C$, amino, alkylamino, dialkylamino, nitro, cyano, $SO_2$, —C(O)$R^G$, —C(O)O$R^G$, —OC(O)$R^G$, —OC(O)O$R^G$, —OC(O)N($R^G$)$_2$, —N($R^G$)C(O)$R^G$, —OSi($R^G$)$_3$—O$R^G$, —SO$_2$N(alkyl)$_2$, —O-(alkyl)$^{1-4}$-C(O)$R^G$ and —O-(alkyl)$_{1-4}$-C(O)O$R^G$;

$R^5$ is selected from the group consisting of hydrogen, alkyl, halogenated alkyl, aryl, aralkyl;

alternatively, $R^3$ and $R^5$ combine to form a six membered ring;

provided that when ----- is a double bond, X is O,

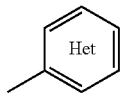

is a six membered heteroaryl ring structure containing one to two nitrogen atoms, and $R^1$ and $R^2$ are taken together with the carbon atom to which they are bound to form C(O), then at least one of n or m is an integer selected from 1 to 4;

provided further that when ----- is a single bond, X is O,

is a six membered heteroaryl ring structure containing one to two nitrogen atoms, $R^1$ is hydrogen and $R^2$ is alkyl, then at least one of n or m is an integer selected from 1 to 4;

provided further that when ----- is a single bond, X is O,

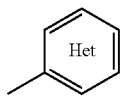

is a six membered heteroaryl ring structure containing one to two nitrogen atoms, $R^1$ is hydrogen, $R^2$ is alkyl, n is 1 and m is 1, then $R^3$ and $R^4$ are other than methoxy or ethoxy;

provided further that when ----- is a double bond, X is O,

is a six membered heteroaryl ring structure containing one to two nitrogen atoms, $R^1$ and $R^2$ are taken together with the carbon atom to which they are bound to form C(O), n is 0 and m is 2, then each $R^4$ is not hydroxy or alkoxy.

provided further that when ----- is a double bond, X is O,

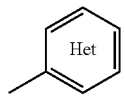

is a six membered heteroaryl ring structure containing one to two nitrogen atoms, $R^1$ and $R^2$ are taken together with the carbon atom to which they are bound to form C(O), one of $R^3$ groups and $R^5$ group are combined into a six membered ring cyclic structure, then at least one of n or m is an integer selected from 1 to 4;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more estrogen receptors in a subject in need thereof comprising administering to the subject a therapeutically effective amount of any of the compounds or pharmaceutical compositions described above.

Illustrating the invention is a method of contraception comprising administering to a subject in need thereof co-therapy with a therapeutically effective amount of a compound of formula (I) with a progestogen or progestogen antagonist.

Another example of the invention is the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) a degenerative brain disorder, (h) cardiovascular disease, (i) cerebrovascular disease (j) breast cancer, (k) endometrial cancer, (l) cervical cancer, (m) prostate cancer, (n) benign prostatic hyperplasia, (o) endometriosis, (p) uterine fibroids, (q) osteoarthritis and for (r) contraception in a subject in need thereof.

DETAILED DESCRIPTION OF THE INVENTION

The present invention is directed to a compound of formula (I)

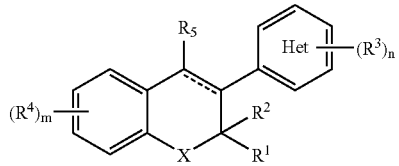

wherein X, $R^1$, $R^2$, $R^3$, $R^4$, $R^5$,

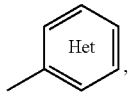

m, and n are as defined above, useful for the treatment of disorders mediated by an estrogen receptor. More particularly, the compounds of the present invention are useful for the treatment and prevention of disorders mediated by the estrogen-α and estrogen-β receptors. More preferably, the compounds of the present invention are tissue selective estrogen receptor modulators.

The compounds of the present invention are useful in the treatment of disorders associated with the depletion of estrogen, hormone sensitive cancers and hyperplasia, endometriosis, uterine fibroids, osteoarthritis and as contraceptive agents, alone or in combination with a progestogen or progestogen antagonist.

More particularly, the compounds of the present invention are useful in the treatment of a condition or disorder selected from the group consisting of hot flashes, vaginal dryness, osteopenia, osteoporosis, hyperlipidemia, loss of cognitive function, degenerative brain diseases, cardiovascular diseases, cerebrovascular diseases, cancer or hyperplasia of the breast tissue, cancer or hyperplasia of the endometrium, cancer or hyperplasia of the cervix, cancer or hyperplasia of the prostate, endometriosis, uterine fibroids and osteoarthritis; and as a contraceptive agent. Preferably, the disorder is selected from the group consisting of osteoporosis, hot flashes, vaginal dryness, breast cancer, and endometriosis.

In the compound of formula (I), the relative orientation of the groups $R^1$ and $R^2$ is not intended to be fixed, rather both possible orientations of the groups are intended to be included within the definition of the compound of formula (I).

In an embodiment of the present invention are compounds of formula (I) wherein X is O. In another embodiment of the present invention are compounds of formula (I) wherein X is S.

In an embodiment of the present invention

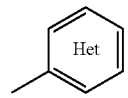

is selected from the group consisting of pyridinyl, oxy-pyridinyl, pyrimidinyl, oxy-pyrimidinyl, pyrazinyl or oxy-pyrazinyl. More preferably

is selected from the group consisting of pyridinyl or pyrimidinyl. More preferably

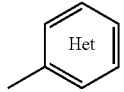

still is selected from the group consisting of m-pyridinyl, p-pyridinyl and p-dimethoxy-pyrimidinyl.

In an embodiment of the present invention $R^1$ is selected from the group consisting of hydrogen, lower alkyl, aryl or aralkyl; wherein the aryl or aralkyl group is optionally substituted with one to two substituents independently selected from halogen, hydroxy, lower alkyl, lower alkoxy, $NO_2$, CN, and $CO_2H$. More preferably, $R^1$ is selected from the group consisting of hydrogen and lower alkyl. More preferably still, $R^1$ is selected from the group consisting of hydrogen and methyl.

In an embodiment of the present invention $R^2$ is selected from the group consisting of hydroxy, lower alkyl, aryl or aralkyl; wherein the aryl or aralkyl is optionally substituted with one to two substituents independently selected from the group consisting of halogen, hydroxy, lower alkyl, lower alkoxy, $NO_2$, CN, $CO_2H$, $R^C$, $-OR^C$, $-NR^DR^E$, -(alkyl)$_{0-4}$-C(O)NR$^D$R$^E$ and -(alkyl)$_{0-4}$-(Q)$_{0-1}$-(alkyl)$_{0-4}$-NR$^D$R$^E$.

Preferably, $R^2$ is selected from the group consisting of hydroxy, lower alkyl, aryl and aralkyl; wherein the aryl or aralkyl is optionally substituted with one to two substituents independently selected from halogen, hydroxy, lower alkyl, lower alkoxy, $NO_2$, CN, $CO_2H$, $R^C$, $-OR^C$ or $-NR^DR^E$;

wherein $R^C$ is selected from the group consisting of alkyl, cycloalkyl, cycloalkyl-alkyl, aryl or aralkyl; wherein the cycloalkyl, cycloalkyl-alkyl, aryl or aralkyl group is optionally substituted with one or more substituents independently selected from halogen, hydroxy, alkyl, alkoxy, $NO_2$, CN, $CO_2H$, $R^C$, $NR^DR^E$, -(alkyl)$_{0-4}$-C(O)—NR$^D$R$^E$ or -(alkyl)$_{0-4}$-(Q)$_{0-1}$-(alkyl)$_{0-4}$-NR$^D$R$^E$;

wherein Q is selected from the group consisting of O, S, NH, N(alkyl) and —CH═CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano.

More preferably, $R^2$ is selected from the group consisting of hydroxy, aryl, 4-(1-heterocycloalkyl-alkoxy)-phenyl, 4-(di(alkyl)amino-alkoxy)-phenyl, 4-(di(alkyl)amino)-phenyl and 4-aralkyloxy-phenyl. More preferably still, $R^2$ is selected from the group consisting of hydroxy, phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl, 4-(dimethylamino)-phenyl, 4-benzyloxyphenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl, 4-(dimethylamino)-phenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(diethylamino-ethoxy)-phenyl, 4-(dimethylamino-ethoxy)-phenyl and 4-(dimethylamino)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepinyl-ethoxy)-phenyl, 4-(dimethylamino-ethoxy)-phenyl and 4-(dimethylamino)-phenyl.

In an embodiment of the present invention are compounds of formula (I) wherein $R^1$ and $R^2$ are taken together with the carbon atom to which they are bound to form C(O).

In an embodiment of the present invention $R^3$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$ —O$R^G$, —O-(alkyl)$_{1-4}$-C(O)$R^G$ and —O-(alkyl)$_{1-4}$-C(O)O$R^G$.

Preferably, $R^3$ is selected from the group consisting of hydroxy, $R^C$, —OC(O)$R^G$, —OC(O)O$R^G$, —OC(O)N($R^G$)$_2$, —OSi($R^G$)$_3$—O$R^G$, —O-(alkyl)$_{1-4}$C(O)$R^G$ and —O-(alkyl)$_{1-4}$- C(O)O$R^G$.

More preferably, $R^3$ is selected from the group consisting of halogen, hydroxy, lower alkoxy, (lower alkyl-di(lower alkyl))-silyloxy, —OC(O)-(lower alkyl), —OC(O)—C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl. More preferably still $R^3$ is selected from the group consisting of fluoro, hydroxy, methoxy, t-butyl-dimethyl-silyloxy, —OC(O)-t-butyl, —OC(O)—C(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl. More preferably still, $R^3$ is selected from the group consisting of hydroxy and —OC(O)-t-butyl.

In an embodiment of the present invention $R^G$ is selected from hydrogen, lower alkyl, aryl, aralkyl and 1,7,7-trimethyl-2-oxabicyclo[2.2.1]heptan-3-one; wherein the alkyl, aryl or aralkyl group is optionally substituted with one to two substituents independently selected from lower alkyl, halogenated lower alkyl, lower alkoxy, halogen, hydroxy, nitro, cyano, —OC(O)-(lower alkyl) and —C(O)O-(lower alkyl).

In another embodiment of the present invention two $R^G$ groups are taken together with the nitrogen atom to which they are bound to form a 5 to 6 membered heterocycloalkyl group; wherein the heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano.

In an embodiment of the present invention $R^4$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$ —O$R^G$, —O-(alkyl)$_{1-4}$-C(O)$R^G$ and —O-(alkyl)$_{1-4}$-C(O)O$R^G$.

Preferably $R^4$ is selected from the group consisting of hydroxy, $R^C$, —OC(O)$R^G$, —OC(O)O$R^G$, —OC(O)N($R^G$)$_2$, —OSi($R^G$)$_3$—O$R^G$, —O-(alkyl)$_{1-4}$-C(O)$R^G$ and —O-(alkyl)$_{1-4}$-C(O)O$R^G$.

More preferably, $R^4$ is selected from the group consisting of hydroxy, lower alkoxy, (lower alkyl-(di(lower alkyl))-silyloxy, —OC(O)-(lower alkyl), —OC(O)—C(phenyl)-OC(O)-(lower alkyl), —OC(O)-(1,7,7-trimethyl-2-oxabicyclo [2.2.1]heptan-3-one) and —OC(O)—C(CH$_3$)(CF$_3$)-phenyl. More preferably still, $R^4$ is selected from the group consisting of hydroxy, methoxy, t-butyl-dimethyl-silyloxy, —OC(O)-t-butyl, —OC(O)—C(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl. More preferably still, $R^4$ is selected from the group consisting of hydroxy and —OC(O)-t-butyl.

In another embodiment of the present invention $R^5$ is selected from the group consisting of hydrogen, lower alkyl, halogenated alkyl, aryl, aralky. More preferably, $R^5$ is selected from the group consisting of hydrogen, methyl, ethyl, chloromethyl, bromomethyl. More preferably still, $R^5$ is selected from the group consisting of methyl and bromomethyl.

A particularly preferred embodiment of the present invention is directed to the following compound:

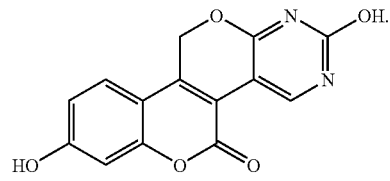

In an embodiment of the present invention, m is an integer selected from 0 to 2. Preferably, m is an integer selected from 0 to 1. More preferably m is 1.

In an embodiment of the present invention, n is an integer selected from 1 to 2. Preferably, n is 1.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, the term "degenerative brain disease" shall include cognitive disorder, dementia, regardless of underlying cause and Alzheimer's disease.

As used herein, the term "cardiovascular disease" shall include elevated blood lipid levels, coronary arthrosclerosis and coronary heart disease.

As used herein, the term "cerebrovascular disease" shall include abnormal regional cerebral blood flow and ischemic brain damage.

As used herein, the term "progestogen antagonist" shall include mifepristone (RU-486), J-867 (Jenapharm/TAP Pharmaceuticals), J-956 (Jenapharm/TAP Pharmaceuticals), ORG-31710 (Organon), ORG-33628 (Organon), ORG-31806 (Organon), onapristone (ZK98299) and PRA248 (Wyeth).

As used herein, unless otherwise noted, "halogen" shall mean chlorine, bromine, fluorine and iodine.

As used herein, unless otherwise noted, the term "alkyl" whether used alone or as part of a substituent group, include straight and branched chain compositions of one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. Similarly, the group "-(alkyl)$_{0-4}$-", whether alone or as part of a large substituent group, shall me the absence of an alkyl group or the presence of an alkyl group comprising one to four carbon atoms. Suitable examples include, but are not limited to —CH$_2$—, —CH$_2$CH$_2$—, CH$_2$—CH(CH$_3$)—, CH$_2$CH$_2$CH$_2$—, —CH$_2$CH(CH$_3$)CH$_2$—, CH$_2$CH$_2$CH$_2$CH$_2$—, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples include benzyl, phenylethyl, phenylpropyl, naphthylmethyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "cycloalkyl-alkyl" shall mean any lower alkyl group substituted with a cycloalkyl group. Suitable examples include, but are not limited to cyclohexyl-methyl, cyclopentyl-methyl, cyclohexyl-ethyl, and the like.

As used herein, unless otherwise noted, the terms "acyloxy" shall mean a radical group of the formula —O—C (O)—R where R is alkyl, aryl or aralkyl, wherein the alkyl, aryl or aralkyl is optionally substituted. As used herein, the term "carboxylate" shall mean a radical group of the formula —C(O)O—R where R is alkyl, aryl or aralkyl, wherein the alkyl, aryl or aralkyl is optionally substituted.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, unless otherwise noted, the term "heteroaryl-alkyl" shall mean any lower alkyl group substituted with a heteroaryl group. Suitable examples include, but are not limited to pyridyl-methyl, isoquinolinyl-methyl, thiazolyl-ethyl, furyl-ethyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, unless otherwise noted, the term "heterocycloalkyl-alkyl" shall mean any lower alkyl group substituted with a heterocycloalkyl group. Suitable examples include, but are not limited to piperidinyl-methyl, piperazinyl-methyl, piperazinyl-ethyl, morpholinyl-methyl, and the like.

When a particular group is "substituted" (e.g., cycloalkyl, aryl, heteroaryl, heterocycloalkyl), that group may have one or more substituents, preferably from one to five substituents, more preferably from one to three substituents, most preferably from one to two substituents, independently selected from the list of substituents. Additionally when aralkyl, heteroaryl-alkyl, heterocycloalkyl-alkyl or cycloalkyl-alkyl group is substituted, the substituent(s) may be on any portion of the group (i.e. the substituent(s) may be on the aryl, heteroaryl, heterocycloalkyl, cycloalkyl or the alkyl portion of the group.)

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

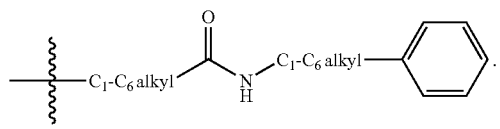

Unless otherwise noted, when naming substituents such as R$^3$ group, the following numbering of the core structure will be applied. The capital letters A, B, C and D will be used to designate specific rings of the tetracyclic core structure.

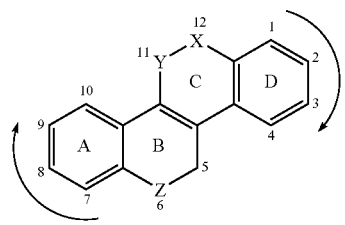

Abbreviations used in the specification, particularly the Schemes and Examples, are as follows
Ac=Acetyl group (—C(O)—CH$_3$)
AD=Alzheimer's disease
CSA=Camphor sulfonic acid
DCC=1,3-Dicyclohexylcarbodiimide
DCM=Dichloromethane
DEAD=Diethylazodicarboxylate
DIAD=Diisopropylazodicarboxylate
Dibal-H=Diisobutyl aluminum hydride
DIC Diisopropylcarbodiimide
DIPEA or DIEA=Diisopropylethylamine
DMAP=N,N-Dimethylaminopyridine
DMF=Dimethyl formamide
ERT=Estrogen replacement therapy
Et=ethyl (i.e. —CH$_2$CH$_3$)
EtOAc=Ethyl acetate
FBS=Fetal bovine serum
HPLC=High pressure liquid chromatography
HRT=Hormone replacement therapy
IPA=Isopropyl alcohol
iPr$_2$NH=Diisopropylamine
LAH=Lithium aluminum hydride
LDA=Lithium Diisopropylamide
LHMDS or LiHMDS or=Lithium Hexamethyldisilazinamide
(TMS)$_2$NLi or LiN(TMS)$_2$
KHMDS=Potassium Hexamethyldisilazinamide
MeOH=Methanol
NaHMDS=Sodium Hexamethyldisilazinamide
NBS=N-Bromosuccinimide
NCS=N-chlorosuccinimide
PBS=Phosphate buffered solution
Ph=Phenyl
PIV or Piv=Pivaloyl
P(Ph)$_3$=Triphenylphosphine
PPTS=Pyridinium p-toluenesulfonate
Rochelle Solution=Aqueous solution of potassium sodium tartrate tetrahydrate
Pybrop
SEM=2-(Trimethylsilyl)ethoxy methyl
SEMCI=2-(Trimethylsilyl)ethoxy methyl chloride
SERM=Selective estrogen receptor modulator
TBAF=Tetra(n-butyl)ammonium fluoride
TBDMS=Tert-butyldimethylsilane
TBS=Tert-butyl-dimethyl-silyl
TBSCI=Tert-butyl-dimethyl-silyl chloride
TEA or Et$_3$N=Triethylamine
TFA=Trifluoroacetic acid
THF=Tetrahydrofuran
TIPSCI=Triisopropylsilyl chloride
TIPSOTf=Triisopropylsilyl trifluoromethane sulfonate
TMS=Trimethylsilyl
TsOH=Tosic acid The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula I and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula I and progestogen would be the amount of the compound of formula I and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula I with a progestogen or progestogen antagonist, wherein the compound(s) of formula I and progestogen or progestogen antagonist are administered by any suitable means, simultaneously, sequentially, separately or in a single pharmaceutical formulation. Where the compound(s) of formula I and the progestogen or progestogen antagonist are administered in separate dosage forms, the number of dosages administered per day for each compound may be the same or different. The compound(s) of formula I and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula I and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

Compounds of formula (I) wherein X, R1, R2, R3, R4, R5, m, n, and

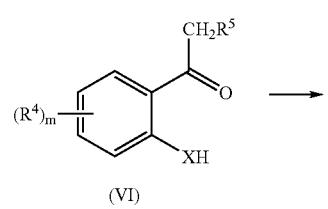

are as described above may be prepared according to the processes outlined in Scheme 1.

Scheme 1

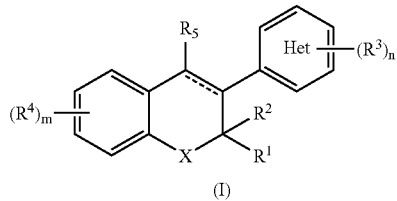

(I)

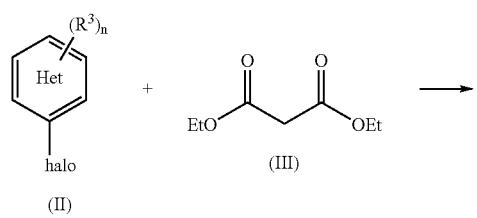

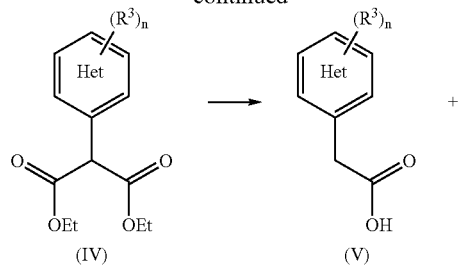

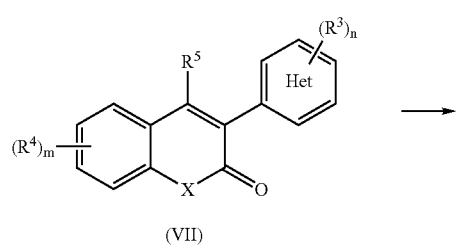

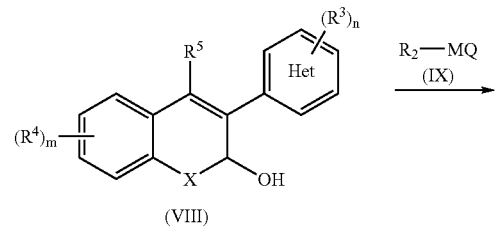

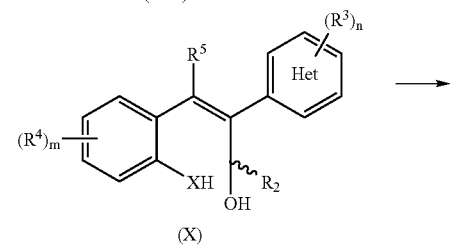

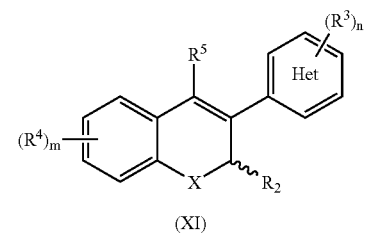

More particularly, a suitably substituted compound of formula (II) is reacted with a compound of formula (III), a known compound, in the presence of an organic base such as NaH, NaOMe, t-BuOK, and the like, in an organic solvent such as THF, dioxlane, DMF, and the like, under the catalysis of copper(I) salt such as CuBr, CuI, CuCl, and the like, at a temperature in the range of about 60 to about 120° C., to yield the corresponding compound of formula (IV).

The compound of formula (IV) is reacted with an inorganic base such as NaOH, KOH or LiOH and the like in a mixed solvent such as such as THF, MeOH, EtOH mixed with water and the like at a temperature in the range of 80 to about 120° C., to yield the corresponding compound of formula (V).

The compound of formula (V) is reacted with a suitably substituted compound of formula (VI), and where X is O or S, a known compound or compound prepared by known methods, in the presence of DCC, DIC, Pybrop and the like, an organic base such as TEA, DIPEA, pyridine, and the like, in an organic solvent such as THF, dioxlane, DCM and the like, at an elevated temperature in the range of about 40 to about 60° C., to yield the corresponding compound of formula (VII).

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

Accordingly, the compound of formula (VII) is reacted with diisobutyl-aluminum hydride, L-selectride, and the like, in an organic solvent such as toluene, benzene, THF, methylene chloride, and the like, at a reduced temperature in the range of about 0 to about −80° C., to yield the corresponding compound of formula (VIII).

The compound of formula (VIII) is reacted with a suitably substituted compound of formula (IX), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (X). Without separation, the compound of formula (X) was then treated with a protic acid such as HCl, $H_2SO_4$, p-toluene sulfonic acid, camphor sulfonic acid (CSA), TFA, and the like or a Lewis acid such as $BF_3$ etherate, $AlCl_3$, $SnCl_4$, and the like, in a solvent such as toluene, methylene chloride, acetonitrile and the like, to yield the corresponding compound of formula (XI).

Alternatively, the compound of formula (X) is treated with a reagent such as triphenylphosphine, tributylphosphine, and the like, or an azodicarboxamide such as DEAD, DIAD, and the like, in a solvent such as toluene, THF, and the like, to yield the corresponding compound of formula (XI).

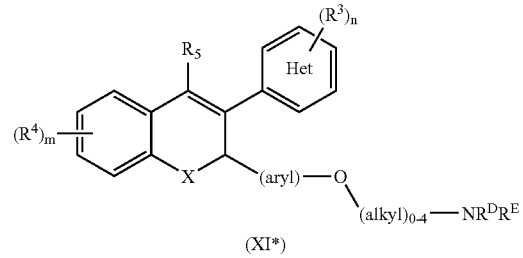

(XI*)

Compounds of formula (XI*) wherein $R^2$ is -(aryl)—O—(alkyl)$_{0-4}$—NR$^D$R$^E$ may be prepared by reacting a suitably substituted compound of formula (XI), wherein the $R^2$ group is -(aryl)—O—(alkyl)$_{0-4}$-Hal (Hal is selected from Cl, Br or I) with a catalytic amount of iodine salt such as NaI, KI, NH$_4$NI, and the like and amine source NHR$^D$R$^E$ such as dimethyl amine, diethyl amine, pyrolidine, piperidine, morpholine and the like, in a solvent such as DMF, DMSO, DMA and the like, to yield the corresponding compound of formula (X). For example, a compound of formula (X*) wherein $R^2$, is-(aryl)—O—(alkyl)$^{0-4}$—NR$^D$R$^E$ may be prepared according to the process outlined in Scheme 2.

One skilled in the art will recognize that it may be necessary and/or desirable to protect one or more of the $R^3$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography.

The compound of formula (XII) may be selectively hydrogenated to yield the corresponding compound of formula (XIII), as shown in Scheme 3.

Scheme 3

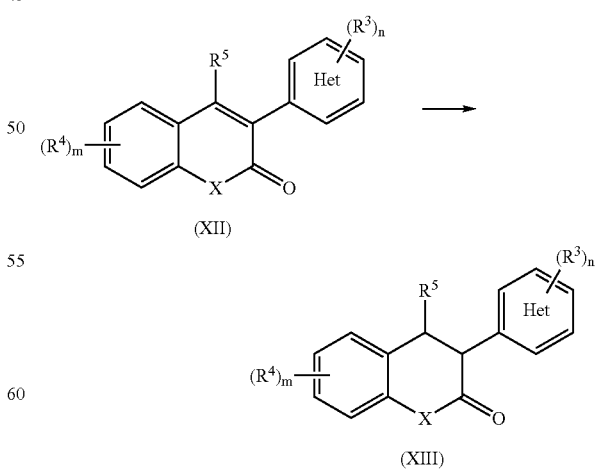

Accordingly, the compound of formula (XII) is reacted with hydrogen gas, at a pressure in the range of about 20 to about 100 psi, in the presence of a metal catalyst such as Pd on Scheme 2

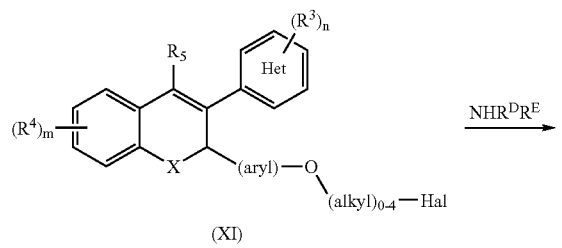

(XI)

C, Pt on C, Raney nickel, Pd(OH)$_2$, and the like, to yield the corresponding compound of formula (XIII), as predominately the cis isomer.

Alternatively, the compound of formula (XII) is reacted with a hydride such as LAH, Cu hydride, SmI$_2$, Stryker's Reagent ([(Ph$_3$P)CuH]$_6$), and the like, in an solvent such as THF, diethyl ether, and the like, at a temperature in the range of about −20 to about 60° C., to yield the corresponding compound of formula (XIII), as predominately the trans isomer.

Alternatively, the compound of formula (XII) is reacted with triethyl silane, in the presence of an acid such as TFA, BF$_3$ etherate, Tin tertachloride, and the like, in an organic solvent such as methylene chloride, toluene, and the like, to yield the corresponding compound of formula (XIII), as a mixture of cis and trans isomers.

Compounds of formula (M) may be prepared according to the processes outlined in Scheme 4.

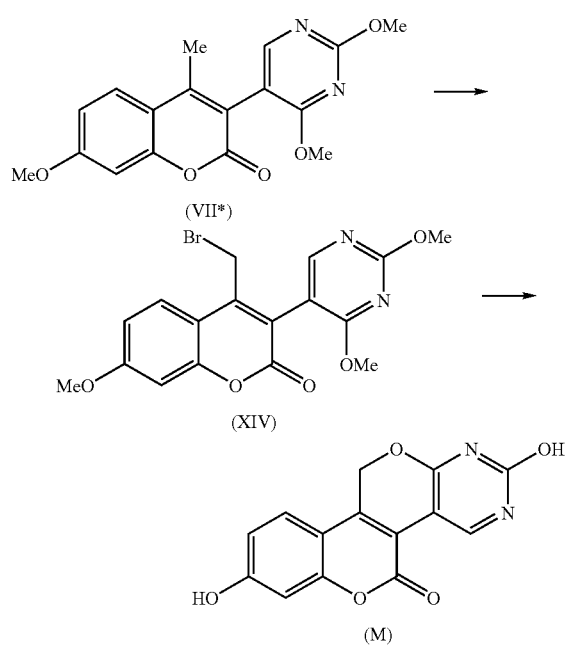

The compound of formula (VII*) is reacted with bromine or a source of bromine or chlorine such as NBS, NCS, and the like, in the presence of a base such as LHMDS, LDA, KHMDS, NaHMDS, and the like, at a reduced temperature in the range of about 30 to about −78° C., to yield the corresponding compound of formula (XIV).

Alternatively, the compound of formula (VII*) is reacted with a radical brominating agent such as NBS, CBrCl$_3$, NaBrO$_3$ in combination with NaHSO$_3$, and the like or a radical chlorinating agent, such as NCS, SO$_2$Cl$_2$, Cl$_2$ gas, t-butyl hypochloride, and the like, preferably a radical brominating agent such as NBS, in the presence of a radical initiator such as benzoyl peroxide, AIBN, and the like and/or in the presence of a light source, such as a tungsten lamp, a 120 Watt light bulb, bright sunshine, and the like, optionally at an elevated temperature in the range of about 50-120° C., to yield the corresponding compound of formula (XIV).

The compound of formula (XIV) is reacted with a de-methylating reagent such as TMS iodide, BBr$_3$, AlCl$_3$ with ethanethiol, and the like, in an chlorinated solvent such as methylene chloride, chloroform, dichloroethane, and the like, followed by a weak base treatment, such as K$_2$CO$_3$, Na$_2$CO$_3$, 1 N NaOH, 1N KOH and the like to yield the corresponding compound of formula (M).

Alternatively, the compound of formula (XIV) is reacted with a de-methylating reagent such as pyridine hydrochloride, pyridine hydrobromide, pyridine hydroiodide, and the like, optionally in an organic solvent such as xylene, acetic acid, and the like, at an elevated temperature in the range of about 170 to about 220° C., followed by a weak base treatment, such as K$_2$CO$_3$, Na$_2$CO$_3$, 1 N NaOH, 1N KOH and the like to yield the corresponding compound of formula (M).

One skilled in the art will recognize that it may be necessary and/or desirable to protect one or more of the R$^3$ and/or R$^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds of the instant invention to treat disorders mediated by an estrogen receptor may be determined according to the procedures described in Examples 1-43, and herein.

The present invention therefore provides a method of treating disorders mediated by an estrogen receptor in a subject in need thereof which comprises administering any of the compounds as defined herein in a quantity effective to treat said disorder. The compound may be administered to a patient by any conventional route of administration, including, but not limited to, intravenous, oral, subcutaneous, intramuscular, intradermal and parenteral. The quantity of the compound which is effective for treating a disorder mediated by an estrogen receptor is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by an estrogen receptor described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of a disorder mediated by an estrogen receptor is required.

The daily dosage of the products may be varied over a wide range from 5 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The following Examples are set forth to aid in the understanding of the invention, and are not intended and should not be construed to limit in any way the invention set forth in the claims which follow thereafter.

EXAMPLE 1

1-[2-Hydroxy-4-(2-trimethylsilanyl-ethoxymethoxy)-phenyl]-ethanone

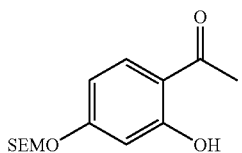

To a solution of 1-(2,4-dihydroxy-phenyl)-ethanone (10.91 g, 71.7 mmoL) in acetone (200 mL) at room temperature was added $K_2CO_3$ (9.9 g, 71.7 mmoL) followed by SEMCI (12.7 mL, 71.7 mmoL). The result mixture was then slightly heated at 50° C. for 2 hours. The solid was removed by filtration. The filtrate was concentrated to give the crude product, which was then purified by silica gel chromatography using 4:1 hexanes:ethyl acetate as eluent to afford the title product as white solid.

$^1$H NMR (CDCl$_3$, δ) 12.60 (s, 1H), 7.62 (d, J=8.5 Hz, 1H), 6.62 (s, 1H), 6.55 (d, J=8.5 Hz, 1H), 5.24 (s, 2H), 3.75 (t, J=11.5 Hz, 2H), 2.58 (s, 3H), 0.95 (t, J=11.5 Hz, 2H), 0.02 (s, 9H). MS, MH$^+$, 282.

EXAMPLE 2

5-Bromo-2,4-bis-(2-trimethylsilanyl-ethoxymethoxy)-pyrimidine

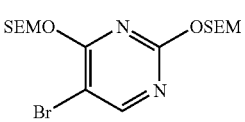

To a solution of 5-bromo-1H-pyrimidine-2,4-dione (5.6 g, 29.3 mmoL) in CH$_2$Cl$_2$ (20 mL) at room temperature was added Et$_3$N (4.2 mL, 29.9 mmoL) followed by SEMCI (4.87 mL, 29.9 mmoL). The result reaction mixture was stirred for 4 hours. Solvent was removed to afford a colorless oil, which was then purified by column chromatography using hexanes: ethyl acetate (4:1 ratio) as eluent to afford the title compound as a slight yellow oil.

$^1$H NMR (CDCl$_3$, δ) 7.65 (s, 1H), 7.25 (s, 1H), 5.46 (s, 2H), 5.15 (s, 2H), 3.70 (t, J=9.5 Hz, 2H), 3.62 (t, J=9.5 Hz, 2H), 0.95 (t, J=9.5 Hz, 4H), 0.03 (s, 9H), 0.02 (s, 9H).

EXAMPLE 3

2-(6-Methoxy-pyridin-3-yl)-malonic acid diethyl ester

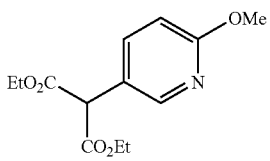

Sodium hydride (60%, 36.2 mmoL, 1.45 g) was added into a solution of 5-bromo-2-methoxy-pyridine (16.5 mmoL, 2.13 mL), copper(I) bromide (32.9 mmoL, 4.72 g) and diethyl malonate (32.9 mmoL, 5.0 mL) in 1,4-dioxlane (20 mL) slowly at room temperature. After the addition, the resulting mixture was heated to 100° C. and stirred overnight. The mixture was then passed through a pad of Celite to remove brown solid. The filtrate was then concentrated in vacuo to afford a brown oil, which was then purified by column chromatography using hexanes:ethyl acetate (4:1~2:1 ratio) as eluent to afford the title compound as a slight yellow oil.

$^1$H NMR (CDCl$_3$, δ) 8.10 (s, 1H), 7.74 (d, J=8.5 Hz, 1H), 6.75 (d, J=8.5 Hz, 1H), 4.55 (s, 1H), 4.25 (m, 4H), 3.95 (s, 3H), 1.25 (m 6H). MS, MH$^+$, 268.

EXAMPLE 4

2-(2,4-Dimethoxy-pyrimidin-5-yl)-malonic acid diethyl ester

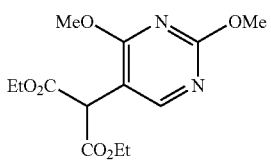

The title product was prepared as a yellow oil according to the procedure described in Example 3 using 5-Iodo-2,4-dimethoxy-pyrimidine as the starting material.

$^1$H NMR (CDCl$_3$, δ) 8.28 (s, 1H), 4.32 (m, 4H), 4.05 (s, 3H), 4.01 (s, 3H), 1.35 (m, 6H), MS, MH$^+$, 298.

EXAMPLE 5

2-[2,4-Bis-(2-trimethylsilanyl-ethoxymethoxy)-pyrimidin-5-yl]-malonic acid diethyl ester

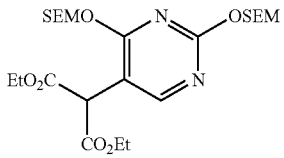

The title product was prepared as a yellow oil according to the procedure described in Example 3 using 5-bromo-2,4-bis-(2-trimethylsilanyl-ethoxymethoxy)-pyrimidine as the starting material.

$^1$H NMR (CDCl$_3$, δ) 7.30 (s, 1H), 7.25 (s, 1H), 5.40 (s, 2H), 5.18 (s, 2H), 4.68 (s, 1H), 4.25 (m, 4H), 3.65 (m, 4H), 1.75 (m, 6H), 1.05 (m, 4H), 0.03 (s, 9H), 0.02 (s, 9H). MS, MH$^+$, 531.

EXAMPLE 6

(6-Methoxy-pyridin-3-yl)-acetic acid

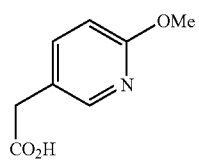

2-(6-Methoxy-pyridin-3-yl)-malonic acid diethyl ester (5.6 g, 21.0 mmoL) prepared in Example 3 was dissolved in 2N NaOH/THF:H$_2$O (1:1) (20 mL). The resulting mixture was heated to reflux for 3 hours. The reaction mixture was then adjusted to pH=1 by concentrated HCl and stirred at room temperature for another 1 hour. The solution was then adjusted to pH=13 by 1N NaOH and extracted with ether. The aqueous phase was acidified to pH=5 by 1N HCl and extracted 3× by ethyl acetate. The combined organic phase was then washed with brine, dried over anhydrous Na$_2$SO$_4$, filtered and concentrated to give the title compound a white solid (2.45, 70%).

$^1$H NMR (CDCl$_3$, δ) 12.5 (br, 1H), 7.91 (s, 1H), 7.46 (d, J=8.1 Hz, 1H), 6.62 (d, J=8.1 Hz, 1H), 3.83 (s, 3H), 3.42 (s, 2H).

EXAMPLE 7

(2,4-Dimethoxy-pyrimidin-5-yl)-acetic acid

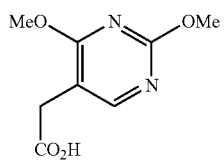

The title product was prepared as a white solid according to the procedure described in Example 6 using 2-(2,4-dimethoxy-pyrimidin-5-yl)-malonic acid diethyl ester as the starting material.

$^1$H NMR (CDCl$_3$, δ) 10.3 (s, br, 1H), 8.15 (s, 1H), 4.05 (s, 6H), 3.48 (s, 2H),

EXAMPLE 8

[2,4-Bis-(2-trimethylsilanyl-ethoxymethoxy)-pyrimidin-5-yl]-acetic acid

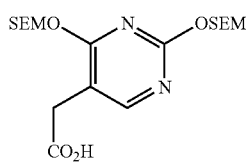

The title product was prepared as a white solid according to the procedure described in Example 6 using 2-[2,4-bis-(2-trimethylsilanyl-ethoxymethoxy)-pyrimidin-5-yl]-malonic acid diethyl ester as the starting material.

$^1$H NMR (CDCl$_3$, δ) 9.48 (br, s, 1H), 7.45 (s, 1H), 5.45 (s, 2H), 5.18 (s, 2H), 3.98 (m, 2H), 3.65 (m, 4H), 0.98 (t, J=11.5 Hz, 4H), 0.03 (s, 9H), 0.02 (s, 9H).

EXAMPLE 9

7-Methoxy-4-methyl-3-pyridin-4-yl-chromen-2-one

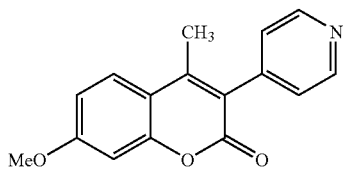

To a solution of 1-(2-hydroxy-4-methoxy-phenyl)-ethanone (2.1 g, 12.0 mmoL) and ☐yridine-4-yl-acetic acid HCl salt (2.0 g, 12.0 mmoL) in CH$_2$Cl$_2$ (20 mL) was added triethyl amine (3.4 mL, 24 mmoL), DMAP (180 mg, 1.2 mmoL) and DCC (3.71 g, 8 mmoL) at room temperature. The mixture was stirred overnight and then heated to reflux for another 2 hours. The resulting solution was concentrated in vacuo and dissolved in ~100 mL ether. The solid was removed by filtration. The filtrate was then concentrated to give the crude material, which was then purified by silica gel chromatography using hexanes ethyl acetate (3:1 to 1:1) as eluent to give the title product as a white solid (1.85 g, 58%).

$^1$H NMR (CDCl$_3$, δ) 8.75 (s, 1H), 7.58 (d, J=6.8 Hz, 1H), 7.25 (d, J=4.32, 2H), 6.90 (d, J=6.8 Hz, 1H), 6.82 (s, 1H), 3.91 (s, 3H), 2.30 (s, 3H), MS, MH$^+$, 267.

EXAMPLE 10

4,7-Dimethyl-3-pyridin-4-yl-chromen-2-one

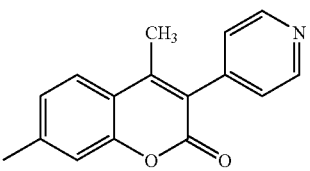

The title product was prepared as a white solid according to the procedure described in Example 9 using 1-(2-hydroxy-4-methyl-phenyl)-ethanone and ☐yridine-4-yl-acetic acid HCl salt as the starting material.

$^1$H NMR (CDCl$_3$, δ) 8.72 (d, J=6.1 Hz, 2H), 7.52 (s, 1H), 7.42 (d, J=8.5 Hz, 1H), 7.23 (d, J=8.5 Hz, 1H), 7.20 (d, J=6.1 Hz, 2H), 2.55 (s, 3H), 2.34 (s, 3H). MS, MH$^+$, 252, MNa$^+$, 274.

EXAMPLE 11

7-Methoxy-4-methyl-3-(1-oxy-pyridin-4-yl)-chromen-2-one

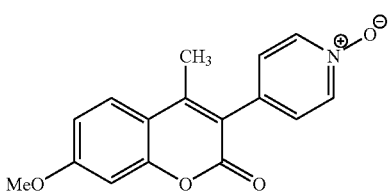

To a solution of in CH$_2$Cl$_2$ was added mCPBA at 0° C. The reaction was slowly warmed to room temperature and washed with sat. Na$_2$S$_2$O$_3$. The aqueous layer was extracted 3× with CH$_2$Cl$_2$. The combined organic phase was washed with sat. NaHCO$_3$, brine, dried over anhydrous Na$_2$SO$_4$, filtered, concentrated to give the crude material, which was then purified by silica gel column chromatography using hexanes:ethyl acetate (1:1 to pure ethyl acetate) to afford the title product as a white solid.

$^1$H NMR (CDCl$_3$, δ) 8.28 (d, J=7.5 Hz, 2H), 7.58 (d, J=7.0 Hz, 1H), 7.26 (d, J=7.5 Hz, 2H), 6.92 (d, J=7.0 Hz, 1H), 6.84 (s, 1H), 3.98 (s, 3H), 2.35 (s, 3H). MS, MH$^+$, 284, MNa$^+$, 306.

EXAMPLE 12

7-Hydroxy-4-methyl-3-pyridin-4-yl-chromen-2-one

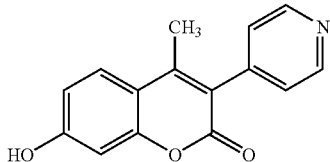

To a solution of 7-methoxy-4-methyl-3-pyridin-4-yl-chromen-2-one (600 mg, 2.24 mmoL) in CH$_2$Cl$_2$ (10 mL) at 0° C. was added EtSH (~1 mL) followed by AlBr$_3$ (6.74 mmoL, 1.80 g). The mixture was slowly warm to room temperature and poured into ice sat. NaHCO$_3$ solution. Extraction was conducted 3× with CH$_2$Cl$_2$. The combined organic layer was washed with brine, dried over anhydrous Na$_2$SO$_4$, filtered and concentrated to give the crude material, which was then purified by silica gel column chromatography using hexanes:ethyl acetate 1:1 as eluent to afford the title product as pale yellow solid.

$^1$H NMR (MeOD, δ) 8.61 (s, br, 1H), 7.72 (d, J=7.5 Hz, 2H), 7.45 (d, J=7.45 Hz, 2H), 7.35 (d, J=5.5 Hz, 1H), 6.86 (d, J=5.5 Hz, 1H), 6.72 (s, 1H), 2.30 (s, 3H). MS, MH$^+$, 254.

EXAMPLE 13

7-(tert-Butyl-dimethyl-silanyloxy)-4-methyl-3-pyridin-4-yl-chromen-2-one

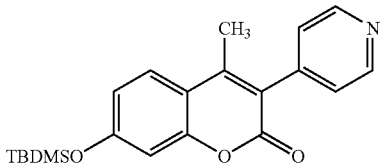

To a solution of 7-hydroxy-4-methyl-3-pyridin-4-yl-chromen-2-one (310 mg, 1.23 mmoL) in DMF (5 mL) was added imidazole (84 mg, 1.23 mmoL) followed by TBDM-SCI (185 mg, 1.23 mmoL) at room temperature. The mixture was stirred for 2 hours and partitioned between ethyl acetate and water. The aqueous layer was extracted 2× with ethyl acetate. The combined organic layer was washed with brine, dried over anhydrous Na$_2$SO$_4$, filtered and concentrated to give the crude material, which was then purified by silica gel column chromatography using hexanes:ethyl acetate 1:1 as eluent to afford the title product as pale yellow solid.

$^1$H NMR (CDCl$_3$, δ) 8.68 (d, J=5.8 Hz, 2H), 7.55 (d, J=8.5 Hz, 1H), 7.24 (d, J=5.8 Hz, 2H), 6.85 (d, J=8.5 Hz, 1H), 6.81 (s, 1H), 2.23 (s, 3H), 1.05 (s, 9H), 0.28 (s, 6H). MS, MH$^+$, 382.

EXAMPLE 14

7-Methoxy-4-methyl-3-pyridin-3-yl-chromen-2-one

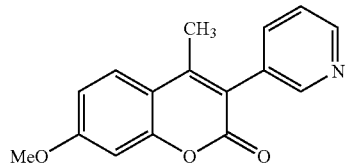

The title product was prepared as a white solid according to the procedure described in Example 9 using 1-(2-hydroxy-4-methoxy-phenyl)-ethanone and □yridine-3-yl-acetic acid HCl as the starting material.

$^1$H NMR (CDCl$_3$, δ) 8.65 (s, 1H), 8.60 (d, J=6.5 Hz, 1H), 7.62-7.49 (m, 3H), 7.02 (d, J=7.5 Hz, 1H), 6.15 (s, 1H), 3.88 (s, 3H), 2.48 (s, 3H), MS, MH$^+$, 267.

EXAMPLE 15

7-Methoxy-3-(6-methoxy-pyridin-3-yl)-4-methyl-chromen-2-one

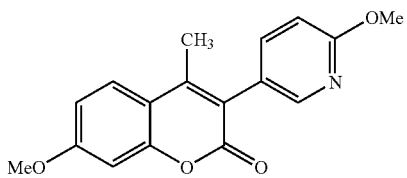

The title product was prepared as a white solid according to the procedure described in Example 9 using 1-(2-hydroxy-4-methoxy-phenyl)-ethanone and (6-methoxy-pyridin-3-yl)-acetic acid as the starting material.

$^1$H NMR (CDCl$_3$, δ) 8.10 (s, 1H), 7.62 (d, J=7.5 Hz, 1H), 7.60 (d, J=7.5 Hz, 1H), 6.92 (d, J=9.2 Hz, 1H), 6.85 (d, J=9.2 Hz, 1H), 6.82 (s, 1H), 4.01 (s, 3H), 3.95 (s, 3H), 2.32 (s, 3H).

EXAMPLE 16

3-(6-Hydroxy-pyridin-3-yl)-7-methoxy-4-methyl-chromen-2-one

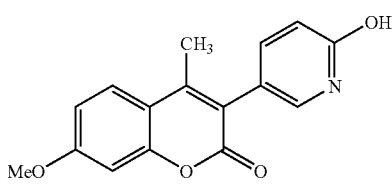

To a solution of 7-methoxy-3-(6-methoxy-pyridin-3-yl)-4-methyl-chromen-2-one in CH$_2$Cl$_2$ (5 mL) at room temperature was added BBr$_3$ (1.0 N, 24.2 mmoL, 24 mL) dropwise. After addition, the reaction was slightly heated to reflux 4 hours. The reaction was quenched with ice sat. NaHCO$_3$, extracted with 3×CH$_2$Cl$_2$, washed with brine, dried over anhydrous Na$_2$SO$_4$, filtered and concentrated to give the crude material. The crude material was re-crystallized in 2:1 hexanes:ethyl acetate to afford the title product as a pale reddish solid.

$^1$H NMR (CDCl$_3$, δ) 7.57 (d, J=7.5 Hz, 1H), 7.42 (d, J=6.5 Hz, 1H), 7.25 (s, 1H), 6.86 (d, J=6.5 Hz, 1H), 6.80 (s, 1H), 6.62 (d, J=7.5 Hz, 1H), 3.82 (s, 3H), 1.98 (s, 3H), MS, MH$^+$, 284.

EXAMPLE 17

3-[6-(tert-Butyl-dimethyl-silanyloxy)-pyridin-3-yl]-7-methoxy-4-methyl-chromen-2-one

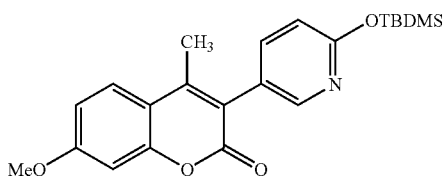

To a solution of 3-(6-hydroxy-pyridin-3-yl)-7-methoxy-4-methyl-chromen-2-one in DMF (5 mL) at room temperature was added imidazole (174 mg, 2.56 mmoL) followed by TBDMSCI (384 mg, 2.56 mmoL). The reaction mixture was stirred for 2 hours and then quenched by sat. NaHCO$_3$. The resulting suspension was extracted 3× with ethyl acetate, washed with brine, dried over anhydrous Na$_2$SO$_4$, filtered and concentrated to give the crude material, which was then purified by silica gel column chromatography using hexanes: ethyl acetate 2:1 as eluent to afford the title product as pale yellow solid.

$^1$H NMR (CDCl$_3$, δ) 8.08 (s, 1H), 7.61 (d, J=6.5 Hz, 1H), 7.55 (d, J=7.5 Hz, 1H), 6.82 (m, 4H), 3.98 (s, 3H), 2.35 (s, 3H), 1.05 (s, 9H), 0.36 (s, 6H).

EXAMPLE 18

3-(6-Methoxy-pyridin-3-yl)-4-methyl-7-(2-trimethylsilanyl-ethoxymethoxy)-chromen-2-one

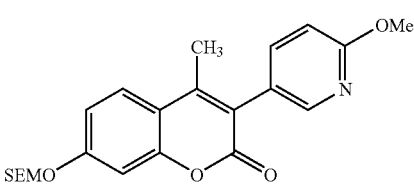

The title product was prepared as a white solid according to the procedure described in Example 9 using 1-[2-hydroxy-4-(2-trimethylsilanyl-ethoxymethoxy)-phenyl]-ethanone and (6-methoxy-pyridin-3-yl)-acetic acid as the starting material.

$^1$H NMR (CDCl$_3$, δ) 8.08 (S, 1H), 7.58 (m, 2H), 7.05 (m, 2H), 6.82 (d, J=6.5 Hz, 1H), 5.28 (s, 2H), 3.98 (s, 3H), 3.76 (t, J=6.5 Hz, 2H), 2.40 (s, 3H), 0.93 (t, J=6.5 Hz, 2H), 0.00 (s, 9H).

EXAMPLE 19

3-(2,4-Dimethoxy-pyrimidin-5-yl)-7-methoxy-4-methyl-chromen-2-one

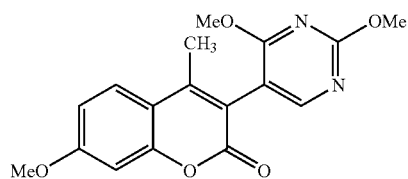

The title product was prepared as a white solid according to the procedure described in Example 9 using 1-(2-hydroxy-4-methoxy-phenyl)-ethanone and (2,4-dimethoxy-pyrimidin-5-yl)-acetic acid as the starting material.

$^1$H NMR (CDCl$_3$, δ) 8.15 (s, 1H), 7.62 (d, J=7.5 Hz, 1H), 6.91 (d, J=7.5 Hz, 1H), 6.88 (s, 1H), 4.05 (s, 3H), 4.00 (s, 3H), 3.91 (s, 3H), 2.25 (s, 3H). MS, MH$^+$, 329, MNa$^+$, 351, [2M+Na]$^+$, 679.

EXAMPLE 20

3-(2,4-Dimethoxy-pyrimidin-5-yl)-4-methyl-7-(2-trimethylsilanyl-ethoxymethoxy)-chromen-2-one

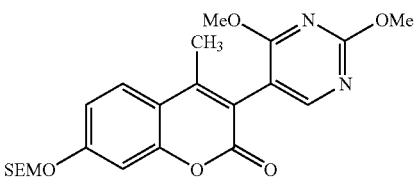

The title product was prepared as a white solid according to the procedure described in Example 9 using 1-[2-hydroxy-4-(2-trimethylsilanyl-ethoxymethoxy)-phenyl]-ethanone and (2,4-dimethoxy-pyrimidin-5-yl)-acetic acid as the starting material.

¹H NMR (CDCl₃, δ) 8.15 (s, 1H), 7.54 (d, J=10.1 Hz, 1H), 7.05 (s, 1H), 7.00 (d, J=10.1 Hz, 1H), 5.28 (s, 2H), 4.08 (s, 3H), 4.01 (s, 3H), 3.75 (t, J=11.5 Hz, 2H), 2.25 (s, 3H), 0.98 (t, J=11.5 Hz, 2H), 0.02 (s, 9H).

EXAMPLE 21

4-Bromomethyl-3-(2,4-dimethoxy-pyrimidin-5-yl)-7-methoxy-chromen-2-one

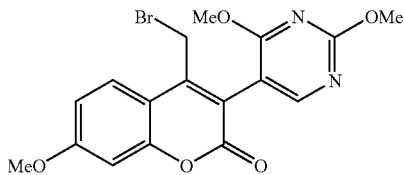

To a solution of 3-(2,4-dimethoxy-pyrimidin-5-yl)-7-methoxy-4-methyl-chromen-2-one (210 mg, 0.64 mmoL) in anhydrous THF (5 mL) at −78° C. was added LiHMDS (1.0 M, 1.28 mmoL, 1.28 mL) dropwise. The resulting reddish solution was stirred at −78° C. for 20 min. To this solution was added NBS (114 mg, 0.64 mmoL) in THF (2 mL) slowly. The reaction was stirred for 2 hours at −78° C. and then quenched with sat. NaHCO₃, warmed to room temperature. THF was removed in vacuo and the residue was partitioned between CH₂Cl₂ and water. The aqueous phase was extracted 3× with CH₂Cl₂. The combined organic layer was washed with brine, dried over anhydrous Na₂SO₄, filtered and concentrated to afford a yellow solid, which was then purified by silica gel column chromatography using hexanes:ethyl acetate (4:1 to 2:1) to afford the title product as a white solid.

¹H NMR (CDCl₃, δ) 8.28 (s, 1H), 7.68 (d, J=7.5 Hz, 1H), 6.95 (dd, J=7.5, 1.5 Hz, 1H), 6.85 (d, J=1.5 Hz, 1H), 4.35 (abq, J=12.5 Hz, 2H), 4.08 (s, 3H), 4.00 (s, 3H), 3.95 (s, 3H).

EXAMPLE 22

2,8-Dihydroxy-11H-6,12-dioxa-1,3-diaza-chrysen-5-one

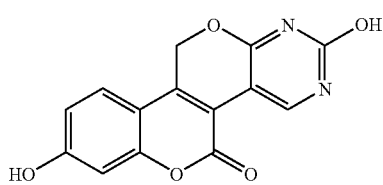

To a solution of 4-bromomethyl-3-(2,4-dimethoxy-pyrimidin-5-yl)-7-methoxy-chromen-2-one (200 mg, 0.492 mmoL) in ClCH₂CH₂Cl (5 mL) at room temperature was added BBr₃ (1.0 N, 2.50 mmoL, 2.5 mL). The result reaction mixture was stirred at room temperature for 30 min and then heated to reflux overnight. The reaction was cooled down and the solvent was removed in vacuo. The residue was dissolved in 10% K₂CO₃ in MeOH:acetone (~1:1, 10 mL) at 0° C., stirring was kept for another 2 hours. The solvent was evaporated to dryness, the residue was dissolved in water (15 mL) and then acidified with dilute hydrochloric acid to about pH 4.

The precipitated brown solid was isolated by filtration, washed with water and dried to yield the title compound.

¹H NMR (d₆DMSO, δ) 11.6 (s, 1H), 8.68 (s, 1H), 7.58 (d, J=8.5 Hz, 1H), 6.91 (d, J=8.5 Hz, 1H), 6.80 (s, 1H), 5.74 (s, 2H).

EXAMPLE 23

7-Methoxy-3-(6-methoxy-pyridin-3-yl)-4-methyl-2H-chromen-2-ol

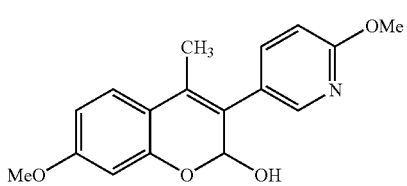

A solution of 7-methoxy-3-(6-methoxy-pyridin-3-yl)-4-methyl-chromen-2-one (430 mg, 1.45 mmol, 1 eq) in toluene (5 mL) was cooled to −78° C. in a 100 mL 3-neck round bottom flask under nitrogen. To the reaction mixture was slowly added a toluene solution of diisobutylaluminum hydride (1.5 mL of 1.0 M, mmol, 1.1 eq), with the temperature of the reaction mixture maintained at less than −70° C. The reaction was stirred for 1 hour, quenched with addition of methanol (0.5 mL). The resulting solution was diluted with dichloromethane, the solution washed with a saturated solution of Rochelle salt, then washed with brine, dried on anhydrous sodium sulphate, filtered and evaporated to yield the crude compound as a yellow solid. The solid was purified by column chromatography using a hexane:ethyl acetate mixture (1:1) to yield the title product as a yellow solid.

¹H NMR (CDCl₃, δ) 8.18 (s, 1H), 7.60 (d, J=7.2 Hz, 1H), 7.32 (d, J=8.0 Hz, 1H), 6.75 (d, J=7.5 Hz, 1H), 6.62 (m, 1H), 6.58 (s, 1H), 5.86 (d, J=6.5 Hz, 1H), 4.05 (d, J=6.5 Hz, 1H), 4.01 (s, 3H), 3.82 (s, 3H), 2.10 (s, 3H). MS, MH⁺, 282, MNa⁺, 314.

EXAMPLE 24

3-[6-(tert-Butyl-dimethyl-silanyloxy)-pyridin-3-yl]-7-methoxy-4-methyl-2H-chromen-2-ol

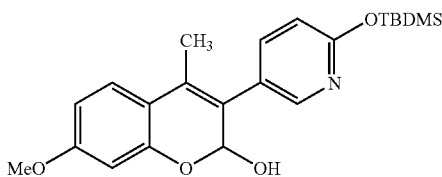

The title product was prepared as a yellow solid according to the procedure described in Example 23 using 3-[6-(tert-butyl-dimethyl-silanyloxy)-pyridin-3-yl]-7-methoxy-4-methyl-chromen-2-one as the starting material.

MS, MH+, 400.

EXAMPLE 25

3-(6-Methoxy-pyridin-3-yl)-4-methyl-7-(2-trimethylsilanyl-ethoxymethoxy)-2H-chromen-2-ol

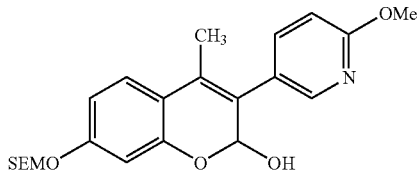

The title product was prepared as a yellow solid according to the procedure described in Example 23 using 3-(6-methoxy-pyridin-3-yl)-4-methyl-7-(2-trimethylsilanyl-ethoxymethoxy)-chromen-2-one as the starting material.

$^1$H NMR (CDCl$_3$, δ) 8.18 (s, 1H), 7.60 (m, 1H), 7.29 (d, J=6.0 Hz, 1H), 6.75 (m, 3H), 5.87 (d, J=5.8 Hz, 1H), 5.20 (s, 2H), 3.95 (s, 3H), 3.71 (t, J=6.5 Hz, 2H), 2.10 (s, 3H), 0.93 (t, J=6.5 Hz, 2H), 0.00 (s, 9H).

EXAMPLE 26

7-Methoxy-4-methyl-3-pyridin-4-yl-2H-chromen-2-ol

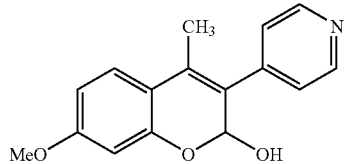

The title product was prepared as a yellow solid according to the procedure described in Example 23 using 7-methoxy-4-methyl-3-pyridin-4-yl-chromen-2-one as the starting material.

$^1$H NMR (CDCl$_3$, δ) 8.52 (d, J=5.5 Hz, 2H), 7.33 (d, J=5.5 Hz, 2H), 7.30 (d, J=7.0 Hz, 1H), 6.62 (m, 2H), 5.98 (s, 1H), 5.92 (br, s, 1H), 3.85 (s, 3H), 2.18 (s, 3H). MS, MH$^+$, 270.

EXAMPLE 27

7-(tert-Butyl-dimethyl-silanyl)-4-methyl-3-pyridin-4-yl-2H-chromen-2-ol

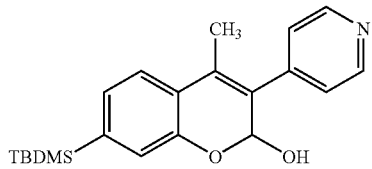

The title product was prepared as a yellow solid according to the procedure described in Example 23 using 7-(tert-butyl-dimethyl-silanyloxy)-4-methyl-3-pyridin-4-yl-chromen-2-one as the starting material.

$^1$H NMR (CDCl$_3$, δ) 8.48 (d, J=6.5 Hz, 2H), 7.33 (d, J=6.5 Hz, 2H), 7.21 (d, J=7.5 Hz, 1H), 6.55 (m, 2H), 5.75 (s, 1H), 5.65 (br, s, 1H), 2.04 (s, 3H) 1.05 (s, 9H), 0.28 (s, 6H). MS, MH$^+$, 354.

EXAMPLE 28

3-(2,4-Dimethoxy-pyrimidin-5-yl)-4-methyl-7-(2-trimethylsilanyl-ethoxymethoxy)-2H-chromen-2-ol

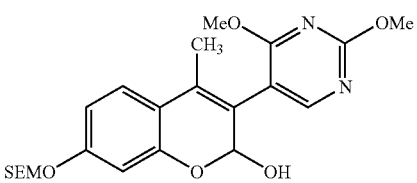

The title product was prepared as a yellow solid according to the procedure described in Example 23 using 3-(2,4-dimethoxy-pyrimidin-5-yl)-7-methoxy-4-methyl-chromen-2-one as the starting material.

$^1$H NMR (CDCl$_3$, δ) 8.15 (s, 1H), 7.28 (d, J=8.5 Hz, 1H), 6.78 (d, J=8.5 Hz, 1H), 6.72 (d, J=6.0 Hz, 1H), 5.88 (d, J=9.5 Hz, 1H), 5.20 (s, 2H), 4.02 (s, 3H), 4.00 (s, 3H), 3.71 (t, J=9.5 Hz, 1H), 1.98 (s, 3H), 0.95 (t, J=9.5 Hz, 2H), 0.02 (s, 9H).

EXAMPLE 29

2-(tert-Butyl-dimethyl-silanyloxy)-5-{2-[4-(2-chloro-ethoxy)-phenyl]-7-methoxy-4-methyl-2H-chromen-3-yl}-pyridine

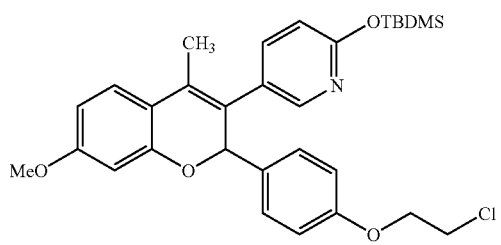

In a single neck, 100 mL round bottom flask was dissolved and stirred 1-(2-chloro-ethoxy)-4-iodo-benzene (530 mg, 1.88 mmol, 5.0 eq), in tetrahydrofuran (5 mL) under nitrogen, and the mixture cooled to –78° C. After 5 minutes of stirring, a hexane solution of n-BuLi (0.75 mL of 2.5 M, 1.88 mmol, 5.0 eq) was added via syringe. The reaction mixture was then stirred for 30 min at about –78° C. A tetrahydrofuran solution of 3-[6-(tert-butyl-dimethyl-silanyloxy)-pyridin-3-yl]-7-methoxy-4-methyl-2H-chromen-2-ol (150 mg, 0.376 mmol, 1 eq, in 2 mL), prepared as in Example 24, was then added, the cooling bath was removed and the reaction mixture was allowed to warm to room temperature overnight. After about 18 hours, the reaction was worked-up with addition of saturated ammonium acetate solution and extraction with ethyl ether. The combined organic extracts were washed with brine and water, dried with anhydrous sodium sulphate, filtered and evaporated to yield a sticky semisolid residue. To this solid was added 0.2 mL HCl in 10 mL toluene at room temperature. The mixture was stirred for 2 hours at room temperature. The reaction was worked-up with sodium bicarbonate washing and extraction with ethyl acetate three times. The combined organic extracts were washed with brine and water, dried with anhydrous sodium sulphate, filtered and evaporated to yield a brown oil. The title product was isolated as a white semisolid foam via chromatography on silica gel eluted with 1:1 hexanes:ethyl acetate as eluent.

$^1$H NMR (CDCl$_3$, δ) 7.75 (s, 1H), 7.15 (d, J=6.5 Hz, 1H), 7.10 (d, J=8.5 Hz, 2H), 7.01 (d, J=6.5 Hz, 1H), 6.60 (d, J=8.5 Hz, 2H), 6.55 (d, J=6.5 Hz, 1H), 6.25 (d, J=7.1 Hz, 1H), 6.11 (s, 1H), 5.61 (s, 1H), 4.02 (t, J=9.5 Hz, 2H), 3.78 (s, 3H), 3.55 (t, J=9.5 Hz, 2H), 1.95 (s, 3H), 0.78 (s, 3H), 0.02 (s, 6H). MS, MH$^+$, 424.

EXAMPLE 30

5-[2-[4-(2-Chloro-ethoxy)-phenyl]-4-methyl-7-(2-trimethylsilanyl-ethoxymethoxy)-2H-chromen-3-yl]-2-methoxy-pyridine

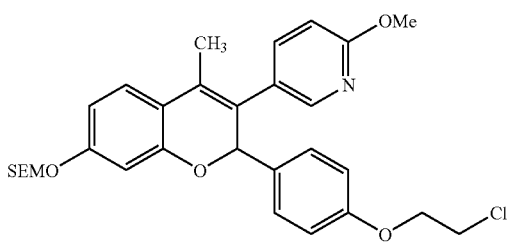

The title product was prepared as a white solid according to the procedure described in Example 29 using 3-(6-methoxy-pyridin-3-yl)-4-methyl-7-(2-trimethylsilanyl-ethoxymethoxy)-2H-chromen-2-ol as the starting material.

$^1$H NMR (CDCl$_3$, δ) 8.00 (s, 1H), 7.35-7.15 (m, 6H), 6.80 (d, J=6.5 Hz, 2H), 6.70 (m, 2H), 6.50 (s, 1H), 5.70 (s, 1H), 5.18 (s, 2H), 4.15 (t, J=4.5 Hz, 2H), 3.90 (s, 3H), 3.75 (t, J=6.5 Hz, 2H), 2.10 (s, 3H), 1.25 (t, J=4.5 Hz, 2H), 0.95 (t, J=6.5 Hz, 2H), 0.00 (s, 9H).

EXAMPLE 31

5-[2-[4-(2-Chloro-ethoxy)-phenyl]-4-methyl-7-(2-trimethylsilanyl-ethoxymethoxy)-2H-chromen-3-yl]-2,4-dimethoxy-pyrimidine

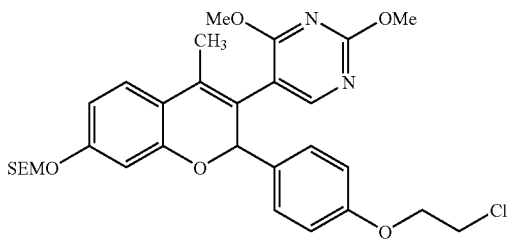

The title product was prepared as a white solid according to the procedure described in Example 29 using 3-(2,4-dimethoxy-pyrimidin-5-yl)-4-methyl-7-(2-trimethylsilanyl-ethoxymethoxy)-2H-chromen-2-ol as the starting material $^1$H NMR (CDCl$_3$, δ) 7.82 (s, 1H), 7.27 (d, J=6.5 Hz, 1H), 7.22 (d, J=9.5 Hz, 2H), 6.82 (d, J=9.5 Hz, 2H), 6.62 (d, J=6.5 Hz, 1H), 6.48 (s, 1H), 5.85 (s, 1H), 5.21 (s, 2H), 4.15 (t, J=8.5 Hz, 2H), 4.03 (s, 3H), 4.01 (s, 3H), 3.76 (t, J=10.5 Hz, 2H), 3.70 (t, J=10.5 Hz, 2H), 1.99 (s, 3H), 0.95 (t, J=8.5 Hz, 2H), 0.03 (s, 9H). MS, MH$^+$, 586.

EXAMPLE 32

4-Methyl-2-[4-(2-piperidin-1-yl-ethoxy)-phenyl]-3-pyridin-4-yl-2H-chromen-7-ol

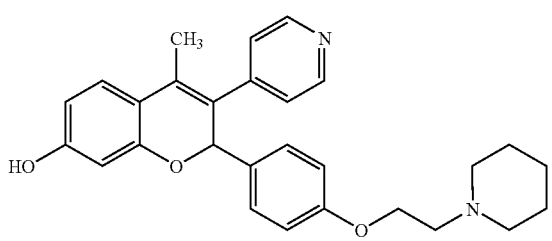

To a solution of 4-[2-(piperidin-1-yl)-ethoxy]-iodobenzene (2.56 g, 7.73 mmol, 3 eq), in tetrahydrofuran (10 mL) under argon at −78° C. was added dropwise isopropylmagnesium bromide (3.6 mL of 2.13 M, 7.73 mmol, 3 eq). The reaction mixture was then stirred for 2 hours at about −78° C. A tetrahydrofuran solution of 7-(tert-butyl-dimethyl-silanyl)-4-methyl-3-pyridin-4-yl-2H-chromen-2-ol (950 mg, 2.58 mmol, 1 eq, in 5 mL), prepared as in Example 27, was then added, the cooling bath was removed and the reaction mixture was allowed to warm to room temperature overnight. After about 18 hours, the reaction was worked-up with addition of saturated ammonium acetate solution (15 mL) and extraction with ethyl ether (2×). The combined organic extracts were washed with brine and water, dried with anhydrous sodium sulphate, filtered and evaporated to yield a sticky semisolid residue. To this solid in THF at room temperature was added 0.5 mL HCl in MeOH. The mixture was stirred for 30 min and quenched with sat. NaHCO$_3$, partitioned between CH$_2$Cl$_2$ and water. The aqueous layer was extracted 3× with CH$_2$Cl$_2$. The combined organic phase was washed with brine, dried over anhydrous Na$_2$SO$_4$, filtered and concentrated to afford the crude material. The title product was isolated as a viscous, colorless, semisolid foam via chromatography on silica gel eluted with 3% methanol/dichloromethane.

$^1$H NMR (CDCl$_3$, δ) 7.45 (d, J=6.4 Hz, 1H), 7.25 (d, J=8.5 Hz, 2H), 7.15 (d, J=8.0 Hz, 2H), 6.81 (d, J=8.0 Hz, 2H), 6.62 (d, J=8.5 Hz, 2H), 6.40 (d, J=6.4 Hz, 1H), 6.25 (s, 1H), 5.78 (s, 1H), 4.05 (t, =9.5 Hz, 2H), 2.73 (t, J=9.5 Hz, 2H), 2.55 (m, 4H), 2.08 (s, 3H), 1.55~1.45 (m, 6H). MS, MH$^+$, 443.

EXAMPLE 33

2-Methoxy-5-{7-methoxy-4-methyl-2-[4-(2-piperidin-1-yl-ethoxy)-phenyl]-2H-chromen-3-yl}-pyridine

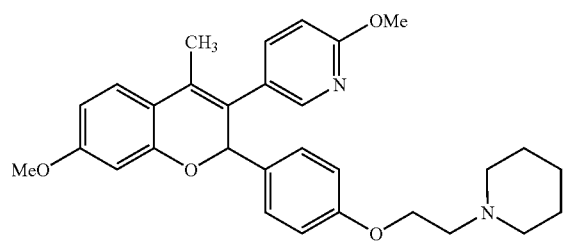

The title product was prepared as a pale yellow solid according to the procedure described in Example 32 using 7-Methoxy-3-(6-methoxy-pyridin-3-yl)-4-methyl-2H-chromen-2-ol as the starting material.

¹H NMR (CDCl₃, δ) 7.98 (s, 1H), 7.55 (d, J=5.5 Hz, 1H), 7.32 (d, J=5.5 Hz, 1H), 7.20 d, J=8.5 Hz, 2H), 7.05 (d, J=5.5 Hz, 1H), 6.70 (d, J=8.5 Hz, 2H), 6.58 (d, J=6.5 Hz, 1H), 6.32 (s, 1H), 5.78 (s, 1H), 4.10 (t, J=10.5 Hz, 2H), 3.95 (s, 3H), 3.78 (s, 3H), 2.75 (t, J=10.5 Hz, 2H), 2.55 (m, 4H), 2.10 (s, 3H), 1.75 (m, 6H). MS, MH+, 487, MNa+, 509.

EXAMPLE 34

5-{7-Methoxy-4-methyl-2-[4-(2-piperidin-1-yl-ethoxy)-phenyl]-2H-chromen-3-yl}-pyridin-2-ol

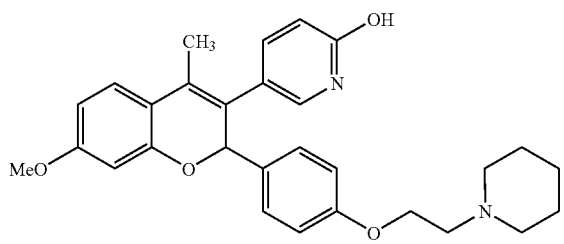

To (80 mg, 0.15 mmoL, 1.0 eq) in DMF (2 mL) was added catalytic amount of KI (15 mg, 0.09 mmoL, 0.6 eq) and piperidine (30 mg, 0.30 mmoL, 2.0 eq). The reaction mixture was heated at 50° C. for 2 hours. CH₂Cl₂ and water were added, the organic layer was separated and the aqueous layer re-extracted with dichloromethane. The combined organic extracts were washed with brine, dried (anhydrous sodium sulphate), filtered and evaporated in vacuo. The residue was purified by chromatography on silica gel using 2% methanol/dichloromethane as an eluent to yield the title product as a crystalline solid.

¹H NMR (CDCl₃, δ) 8.01 (s, 1H), 7.81 (d, J=6.5 Hz, 1H), 7.42 (d, J=6.5 Hz, 1H), 7.30 (d, J=7.5 Hz, 1H), 7.20 (d, J=7.5 Hz, 2H), 6.68 (d, J=7.5 Hz, 2H), 6.42 (d, J=6.5 Hz, 1H), 6.25 (s, 1H), 5.72 (s, 1H), 4.23 (t, J=9.5 Hz, 2H), 3.98 (s, 3H), 3.68 (t, J=9.5 Hz, 2H), 2.70 (m, 4H), 2.15 (s, 3H), 1.68 (m 6H). MS, MH⁺, 473, MNa⁺, 495.

EXAMPLE 35

3-(2,4-Dimethoxy-pyrimidin-5-yl)-4-methyl-2-[4-(2-piperidin-1-yl-ethoxy)-phenyl]-2H-chromen-7-ol

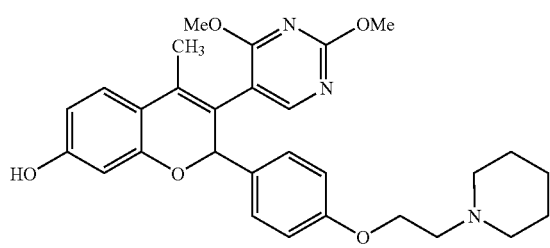

The title product was prepared as a white solid according to the procedure described in Example 34 using 5-[2-[4-(2-Chloro-ethoxy)-phenyl]-4-methyl-7-(2-trimethylsilanyl-ethoxymethoxy)-2H-chromen-3-yl]-2,4-dimethoxy-pyrimidine and piperidine as the starting material.

¹H NMR (CDCl₃, δ) 7.82 (br, s, 1H), 7.24 (d, J=8.2 Hz, 2H), 7.18 (d, J=8.0 z, 1H), 6.80 (d, J=8.2 Hz, 2H), 6.48 (d, J=8.0 Hz, 1H), 6.18 (s, 1H), 5.78 (s, 1H), 4.18 (t, J=9.5 Hz, 2H), 4.05 (s, 3H), 3.98 (s, 3H), 2.95 (t, J=9.5 Hz, 2H), 2.75 (m, 4H), 1.98 (s, 3H), 1.68 (m, 6H), MS, MH⁺, 504, MNa⁺, 526.

EXAMPLE 36

2-[4-(2-Diethylamino-ethoxy)-phenyl]-3-(2,4-dimethoxy-pyrimidin-5-yl)-4-methyl-2H-chromen-7-ol

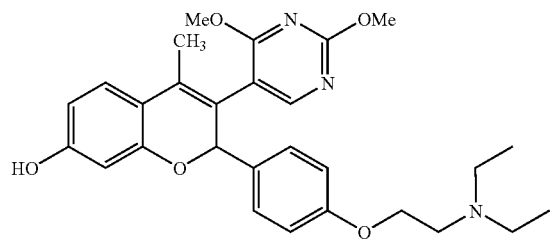

The title product was prepared as a white solid according to the procedure described in Example 34 using 5-[2-[4-(2-Chloro-ethoxy)-phenyl]-4-methyl-7-(2-trimethylsilanyl-ethoxymethoxy)-2H-chromen-3-yl]-2,4-dimethoxy-pyrimidine and diethyl amine as the starting material.

¹H NMR (CDCl₃, δ) 7.82 (s, 1H), 7.25 (d, J=7.5 Hz, 2H), 7.15 (s, 1H), 6.72 (d, J=7.5 Hz, 2H), 6.52 (d, J=6.5 Hz, 1H), 6.48 (d, J=6.5 Hz, 1H), 6.28 (s, 1H), 5.75 (s, 1H), 4.05 (s, 3H), 4.01 (s, 3H), 4.08 (t, J=9.5 Hz, 2H), 2.95 (t, J=9.5 Hz, 2H), 2.60 (q, J=10.5 Hz, 4H), 1.95 (s, 3H), 1.15 (t, J=10.5 Hz, 6H). MS, MH⁺, 492, MNa⁺, 514.

EXAMPLE 37

3-(2,4-Dimethoxy-pyrimidin-5-yl)-4-methyl-2-[4-(2-pyrrolidin-1-yl-ethoxy)-phenyl]-2H-chromen-7-ol

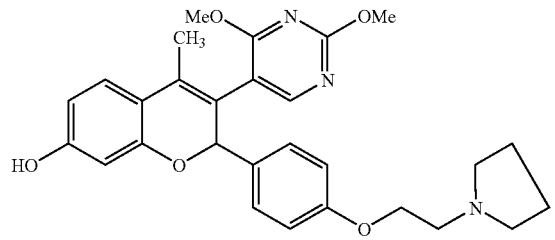

The title product was prepared as a white solid according to the procedure described in Example 34 using 5-[2-[4-(2-Chloro-ethoxy)-phenyl]-4-methyl-7-(2-trimethylsilanyl-ethoxymethoxy)-2H-chrome n-3-yl]-2,4-dimethoxy-pyrimidine and pyrolidine as the starting material.

¹H NMR (CDCl₃, δ) 7.72 (s, 1H), 7.25 (d, J=10.5 Hz, 2H), 7.18 (d, J=8.5 Hz, 1H), 6.85 (d, J=10.5 Hz, 2H), 6.38 (d, J=8.5 Hz, 1H), 6.12 (s, 1H), 5.78 (s, 1H), 4.25 (t, J=10.5 Hz, 2H), 4.01 (s, 3H), 3.95 (s, 3H), 3.51 (t, J=10.5 Hz, 2H), 3.30 (m, 4H), 2.10 (m, 4H), 1.96 (s, 3H). MS, MH⁺, 490, MNa⁺, 512.

EXAMPLE 38

3-(2,4-Dimethoxy-pyrimidin-5-yl)-4-methyl-2-[4-(2-morpholin-4-yl-ethoxy)-phenyl]-2H-chromen-7-ol

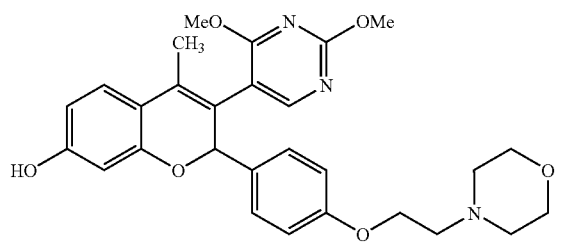

The title product was prepared as a white solid according to the procedure described in Example 34 using 5-[2-[4-(2-Chloro-ethoxy)-phenyl]-4-methyl-7-(2-trimethylsilanyl-ethoxymethoxy)-2H-chromen-3-yl]-2,4-dimethoxy-pyrimidine and morpholine as the starting material.

$^1$H NMR (CDCl$_3$, δ) 7.80 (s, 1H), 7.23 (d, J=6.5 Hz, 2H), 7.10 (s, 1H), 6.72~6.48 (m, 4H), 6.25 (s, 1H), 5.85 (s, 1H), 4.02 (s, 3H), 3.98 (s, 3H), 3.90 (t, J=8.5 Hz, 2H), 3.75 (d, J=9.5 Hz, 4H), 3.56 (t, J=9.5 Hz, 4H), 2.90 (t, J=8.5 Hz, 2H), 2.01 (s, 3H). MS, MH$^+$, 506.

EXAMPLE 39

3-(6-Methoxy-pyridin-3-yl)-4-methyl-2-[4-(2-piperidin-1-yl-ethoxy)-phenyl]-2H-chromen-7-ol

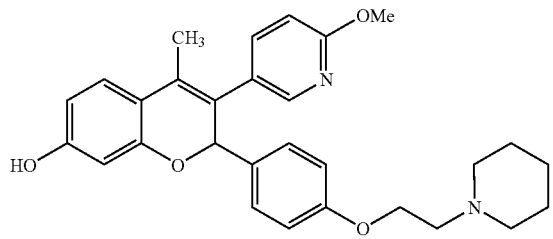

The title product was prepared as a white solid according to the procedure described in Example 34 using 5-[2-[4-(2-chloro-ethoxy)-phenyl]-4-methyl-7-(2-trimethylsilanyl-ethoxymethoxy)-2H-chromen-3-yl]-2-methoxy-pyridine and piperidine as the starting material.

$^1$H NMR (CDCl$_3$, δ) 7.95 (s, 1H), 7.40 (m, 2H), 7.35-7.15 (m, 3H), 6.65 (m, 3H), 6.40 (m, 1H), 6.25 (s, 1H), 5.75 (s, 1H), 4.00 (t, J=2.1 Hz, 2H), 3.90 (s, 3H), 2.75 (m, 2H), 2.60 (m, 4H), 2.00 (s, 3H), 1.65 (m, 4H), 1.45 (m, 2H).

EXAMPLE 40

3-(6-Methoxy-pyridin-3-yl)-4-methyl-2-[4-(2-pyrrolidin-1-yl-ethoxy)-phenyl]-2H-chromen-7-ol

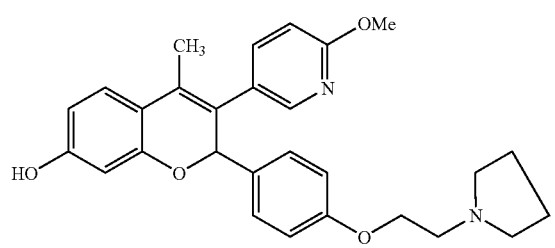

The title product was prepared as a white solid according to the procedure described in Example 34 using 5-[2-[4-(2-chloro-ethoxy)-phenyl]-4-methyl-7-(2-trimethylsilanyl-ethoxymethoxy)-2H-chromen-3-yl]-2-methoxy-pyridine and pyrolidine as the starting material.

$^1$H NMR (CDCl$_3$, δ) 7.90 (s, 1H), 7.30-7.10 (m, 5H), 6.65 (m, 3H), 6.30 (m, 1H), 6.20 (s, 1H), 5.70 (s, 1H), 4.00 (t, J=2.1 Hz, 2H), 3.90 (s, 3H), 2.90 (m, 2H), 2.60 (m, 4H), 2.00 (s, 3H), 1.75 (m, 4H).

Following the procedures described in the Schemes and Examples above, representative compounds of the present invention were prepared, as listed in Tables 1.

TABLE 1

| ID No. | Het—R³ | R⁴ | R⁵ | R¹/R² | Calc. MW. |
|---|---|---|---|---|---|
| 1 | (4-pyridyl) | 8-methoxy | methyl | =O | 267.28 |

TABLE 1-continued

| ID No. | Het-R³ | R⁴ | R⁵ | R¹/R² | Calc. MW. |
|---|---|---|---|---|---|
| 2 | 4-pyridyl | 8-methyl | methyl | =O | 251.28 |
| 3 | 4-pyridyl N-oxide | 8-methoxy | methyl | =O | 283.28 |
| 4 | 4-pyridyl | 8-hydroxy | methyl | =O | 253.25 |
| 5 | 4-pyridyl | 8-(t-butyl-dimethyl-silyloxy) | methyl | =O | 367.51 |
| 6 | 3-pyridyl | 8-methoxy | methyl | =O | 267.28 |
| 7 | 2-OMe-5-pyridyl | 8-methoxy | methyl | =O | 297.31 |
| 8 | 2-OH-5-pyridyl | 8-methoxy | methyl | =O | 283.28 |
| 9 | 2-OTBDMS-5-pyridyl | 8-methoxy | methyl | =O | 397.54 |
| 10 | 2-OMe-5-pyridyl | 8-SEM | methyl | =O | 413.54 |
| 11 | 2,4-diOMe-5-pyrimidinyl | 8-methoxy | methyl | =O | 328.32 |
| 12 | 2,4-diOMe-5-pyrimidinyl | 8-SEM | methyl | =O | 444.55 |

TABLE 1-continued
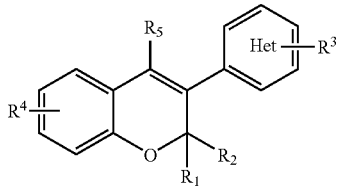
| ID No. | Het—R³ 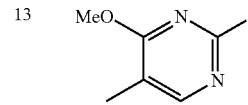 | R⁴ | R⁵ | R¹/R² | Calc. MW. |
|---|---|---|---|---|---|
| 13 | 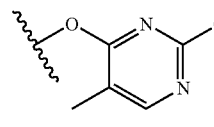 | 8-methoxy | bromomethyl | =O | 407.22 |
| 14 | 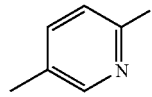 | 8-hydroxy | CH₂ linked to Het— | =O | 284.22 |
| 15 | 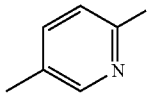 | 8-methoxy | methyl | H/OH | 299.32 |
| 16 | 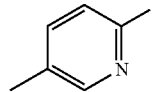 | 8-methoxy | methyl | H/OH | 399.56 |
| 17 |  | 8-SEM | methyl | H/OH | 415.55 |
| 18 |  | 8-methoxy | methyl | H/OH | 269.30 |
| 19 |  | 8-(t-butyl-dimethyl-silyloxy) | methyl | H/OH | 369.53 |
| 20 | 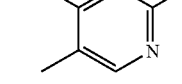 | 8-SEM | methyl | H/OH | 446.57 |
| 21 | 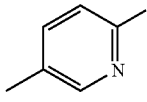 | 8-methoxy | methyl | H/ 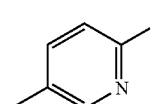 | 538.15 |
| 22 | 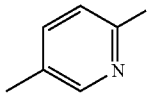 | 8-SEM | methyl | H/ 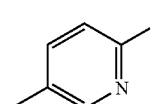 | 554.15 |

TABLE 1-continued

| ID No. | Het—R³ | R⁴ | R⁵ | R¹/R² | Calc. MW. |
|---|---|---|---|---|---|
| 23 | MeO-pyrimidine(Me)-OMe | 8-SEM | methyl | H / 4-(2-chloroethoxy)benzyl | 585.16 |
| 24 | 4-pyridyl | 8-hydroxy | methyl | H / 4-(2-piperidinoethoxy)benzyl | 442.55 |
| 25 | 2-OMe-5-pyridyl | 8-methoxy | methyl | H / 4-(2-piperidinoethoxy)benzyl | 486.60 |
| 26 | 2-OH-5-pyridyl | 8-methoxy | methyl | H / 4-(2-piperidinoethoxy)benzyl | 472.58 |
| 27 | MeO-pyrimidine(Me)-OMe | 8-hydroxy | methyl | H / 4-(2-piperidinoethoxy)benzyl | 503.59 |
| 28 | MeO-pyrimidine(Me)-OMe | 8-hydroxy | methyl | H / 4-(2-diethylaminoethoxy)benzyl | 491.58 |
| 29 | MeO-pyrimidine(Me)-OMe | 8-hydroxy | methyl | H / 4-(2-pyrrolidinoethoxy)benzyl | 489.56 |

TABLE 1-continued

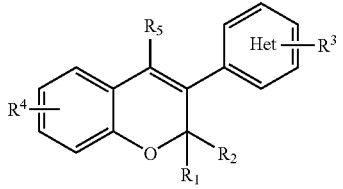

| ID No. | Het―R³ 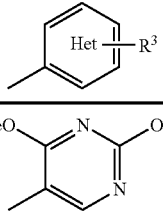 | R⁴ | R⁵ | R¹/R² | Calc. MW. |
|---|---|---|---|---|---|
| 30 | 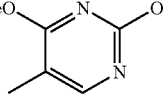 | 8-hydroxy | methyl | H/ 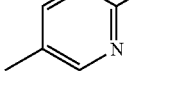 | 505.56 |
| 31 | 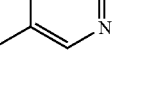 | 8-hydroxy | methyl | H/ | 472.58 |
| 32 | | 8-hydroxy | methyl | H/ | 458.55 |

EXAMPLE 41

MCF-7 Cell Proliferation Assay

This assay was run according to the procedure described by Welshons, et al., (*Breast Cancer Res. Treat*, 1987, 10(2), 169-75), with minor modification.

Briefly, MCF-7 cells (from Dr. C. Jordan, Northwestern University) were maintained in RPMI 1640 phenol red free medium (Gibco) in 10% FBS (Hyclone), supplemented with bovine insulin and non-essential amino acid (Sigma). The cells were initially treated with 4-hydoxyltamoxifen ($10^{-8}$ M) and let stand at 37° C. for 24 hours. Following this incubation with tamoxifen, the cells were treated with compounds at various concentrations.

Compounds to be tested in the agonist mode were added to the culture media at varying concentrations. Compounds to be treated in the antagonist mode were prepared similarly, and 10 nM 17β-estradiol was also added to the culture media. The cells were incubated for 24 hours at 37° C. Following this incubation, 0.1 □Ci of $^{14}$C-thymidine (56 mCi/mmol, Amersham) was added to the culture media and the cells were incubated for an additional 24 hours at 37° C. The cells were then washed twice with Hank's buffered salt solution (HBSS) (Gibco) and counted with a scintillation counter. The increase in the $^{14}$C-thymidine in the compound treated cells relative to the vehicle control cells were reported as percent increase in cell proliferation.

Representative compound of the present invention were tested according to the procedure described above, with results as listed in Table. 2.

TABLE 2

| ID No | Agonist (No.) (nM) | Antagonist (No.) (nM) |
|---|---|---|
| 27 | NA | 843 |
| 28 | NA | 3640 |
| 29 | NA | 1264 |
| 30 | NA | >10000 |
| 31 | NA | 533 |
| 32 | NA | 662 |

NA INDICATES NO DETECTED ACTIVITY AT TEST CONCENTRATION.

EXAMPLE 42

Alkaline Phosphatase Assay in Human Endometrial Ishikawa Cells

This assay was run according to the procedure described by Albert et al., *Cancer Res*, (9910), 50(11), 330-6-10, with minor modification.

Ishikawa cells (from ATCC) were maintained in DMEM/F12 (1:1) phenol red free medium (Gibco) supplemented with 10% calf serum (Hyclone). 24 hours prior to testing, the medium was changed to DMEM/F12 (1:1) phenol red free containing 2% calf serum.

Compounds to be tested in the agonist mode were added to the culture media at varying concentrations. Compounds to be treated in the antagonist mode were prepared similarly, and 10 nM 17β-estradiol was also added to the culture media. The cells were then incubated at 37° C. for 3 days. On the fourth day, the media was remove, 1 volume of 1× Dilution Buffer (Clontech) was added to the well followed by addition of 1 volume of Assay Buffer (Clontech). The cells were then incubated at room temperature for 5 minutes. 1 volume of freshly prepared Chemiluminescence Buffer (1 volume of chemiluminescent substrate (CSPD) in 19 volume Chemiluminescent Enhancer with final concentration of CSPD at 1.25 mM; Sigma Chemical Co.) was added. The cells were incubated at room temperature for 10 minutes and then quantified on a luminometer. The increase of chemiluminescence over vehicle control was used to calculate the increase in alkaline phosphatase activity.

Representative compound of the present invention were tested according to the procedure described above, with results as listed in Table 3.

TABLE 3

| ID No | Agonist (No.) (nM) | Antagonist (No.) (nM) |
|---|---|---|
| 27 | NA | 488 |
| 28 | NA | >10000 |
| 29 | NA | 581 |
| 30 | NA | >10000 |
| 31 | NA | 38 |
| 32 | NA | 72.5 |

NA INDICATES NO DETECTED ACTIVITY AT TEST CONCENTRATION;

EXAMPLE 43

As a specific embodiment of an oral composition, 100 mg of the compound 11, prepared as in Example 11 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

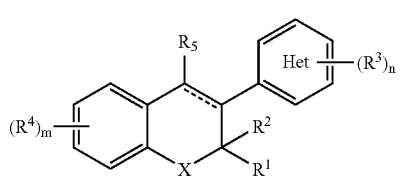

wherein

------represents a single or double bond,

X is selected from the group consisting of O and S;

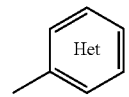

is pyrimidine;

$R^1$ is selected from the group consisting of hydrogen, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^D R^E$, —$NR^D R^E$, $NR^D$—$SO_2$—$R^F$, -(alkyl)$_{0-4}$-C(O)$NR^D R^E$, (alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^D R^E$, $NR^D R^E$, $NR^D$—$SO_2$—$R^F$, -(alkyl)$_{0-4}$-C(O)—$NR^D R^E$, -(alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

wherein Q is selected from the group consisting of O, S, NH, N(alkyl) and —CH=CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

$R^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^D R^E$, —$NR^D R^E$, $NR^D$—$SO_2$—$R^F$, -(alkyl)$_{0-4}$-C(O)$NR^D R^E$, (alkyl)$_{0-4}$-$NR^D$—C(O)—$R^F$, -(alkyl)$_{0-4}$-(Q)$_{0-1}$-(alkyl)$_{0-4}$- $NR^D R^E$, -(alkyl)$_{0-4}$-(Q)$_{0-1}$-(alkyl)$_{0-4}$-C(O)—$OR^F$, -(alkyl)$_{1-4}$-(Q)$_{0-1}$-(alkyl)$_{0-4}$-C(O)—$NR^D R^E$ or -(alkyl)$_{0-4}$- C(O)-(alkyl)$_{0-4}$-C(O)—$OR^F$;

alternatively, $R^1$ and $R^2$ are taken together with the carbon atom to which they are bound to form C(O);

n is an integer selected from 0 to 4;

each $R^3$ is independently selected from the group consisting of halogen, hydroxy, $R^C$, amino, alkylamino, dialkylamino, nitro, cyano, $SO_2$, —C(O)$R^G$, —C(O)$OR^G$, —OC(O)$R^G$, —OC(O)$OR^G$, —OC(O)N($R^G$)$_2$, —N($R^G$)C(O)$R^G$, —OSi($R^G$)$_3$—$OR^G$, —$SO_2$N($R^G$)$_2$, —O-(alkyl)$^{1-4}$-C(O)$R^G$ and —O-(alkyl)$_{1-4}$-C(O)$OR^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, $R^C$, amino, alkylamino, dialkylamino, nitro, cyano, $SO_2$, —C(O)$R^G$, —C(O)$OR^G$, —OC(O)$R^G$, —OC(O)$OR^G$, —OC(O)N($R^G$)$_2$, —N($R^G$)C(O)$R^G$, —OSi($R^G$)$_3$—$OR^G$, —$SO_2$N(alkyl)$_2$, —O-(alkyl)$_{1-4}$-C(O)$R^G$ and —O-(alkyl)$_{1-4}$-C(O)$OR^G$;

$R^5$ is selected from the group consisting of hydrogen, alkyl, halogenated alkyl, aryl, aralkyl;

alternatively, $R^3$ and $R^5$ combined to form six membered ring;

provided that when ----- is a double bond, X is O,

is pyrimidine, and $R^1$ and $R^2$ are taken together with the carbon atom to which they are bound to form C(O), then at least one of n or m is an integer selected from 1 to 4;

provided further that when ----- is a single bond, X is O,

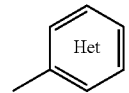

is pyrimidine, $R^1$ is hydrogen and $R^2$ is alkyl, then at least one of n or m is an integer selected from 1 to 4;

provided further that when ----- is a single bond, X is O,

is pyrimidine, $R^1$ is hydrogen, $R^2$ is alkyl, n is 1 and m is 1, then $R^3$ and $R^4$ are other than methoxy or ethoxy;

provided further that when ----- is a double bond, X is O,

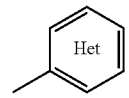

is pyrimidine, $R^1$ and $R^2$ are taken together with the carbon atom to which they are bound to form C(O), n is 0 and m is 2, then each $R^4$ is not hydroxy or alkoxy, provided further that when ----- is a double bond, X is O,

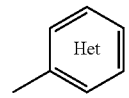

is pyrimidine, $R^1$ and $R^2$ are taken together with the carbon atom to which they are bound to form C(O), $R^3$ and $R^5$ are combined into a six membered ring, then at least one of n or m is an integer selected from 1 to 4, and pharmaceutically acceptable salts thereof.

2. The compound of claim 1, wherein $R^1$ is selected from the group consisting of hydrogen, lower alkyl, aryl or aralkyl; wherein the aryl or aralkyl group is optionally substituted with one to two substituents independently selected from halogen, hydroxy, lower alkyl, lower alkoxy, $NO_2$, CN, and $CO_2H$.

3. The compound of claim 1, wherein $R^2$ is selected from the group consisting of hydroxy, lower alkyl, aryl or aralkyl; wherein the aryl or aralkyl is optionally substituted with one to two substituents independently selected from halogen, hydroxy, lower alkyl, lower alkoxy, $NO_2$, CN, $CO_2H$, $R^C$, —$OR^C$, —$NR^D R^E$, -(alkyl)$_{0-4}$-C(O)$NR^D R^E$ and -(alkyl)$_{0-4}$-(Q)$_{0-1}$-(alkyl)$_{0-4}$-$NR^D R^E$.

4. The compound of claim 1, wherein $R^1$ and $R^2$ are taken together with the carbon atom to which they are bound to form C(O).

5. The compound of claim 1, wherein $R^3$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$—O$R^G$, —O-(alkyl)$^{1-4}$-C(O)$R^G$ and —O-(alkyl)$_{1-4}$-C(O)O$R^G$.

6. The compound of claim 1, wherein $R^4$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$—O$R^G$, —O-(alkyl)$^{1-4}$-C(O)$R^G$ and —O-(alkyl)$_{1-4}$-C(O)O$R^G$.

7. The compound of claim 1, wherein $R^5$ is selected from the group consisting of hydrogen, lower alkyl, halogenated alkyl, aryl, aralky.

8. The compound of claim 1 having the following formula:

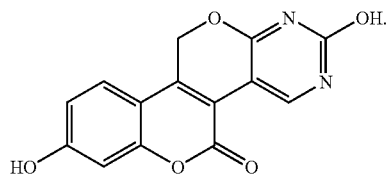

9. A pharmaceutical composition comprising a pharmaceutically acceptable carrier and a compound of claim 1.

* * * * *